US012702729B2

(12) United States Patent
Becker et al.

(10) Patent No.: US 12,702,729 B2
(45) Date of Patent: Aug. 11, 2026

(54) RESORBABLE COMPLEX SHAPE MEMORY POLY(PROPYLENE FUMARATE) STAR SCAFFOLDS FOR 4D PRINTING APPLICATIONS

(71) Applicants: Matthew Becker, Chapel Hill, NC (US); Gaelle Le Fer, Lille (FR)

(72) Inventors: Matthew Becker, Chapel Hill, NC (US); Gaelle Le Fer, Lille (FR)

(73) Assignee: The University of Akron, Akron, OH (US)

( * ) Notice: Subject to any disclaimer, the term of this patent is extended or adjusted under 35 U.S.C. 154(b) by 741 days.

(21) Appl. No.: 18/025,630

(22) PCT Filed: Apr. 27, 2021

(86) PCT No.: PCT/US2021/029353
§ 371 (c)(1),
(2) Date: Mar. 9, 2023

(87) PCT Pub. No.: WO2022/055558
PCT Pub. Date: Mar. 17, 2022

(65) Prior Publication Data

US 2023/0347014 A1 Nov. 2, 2023

Related U.S. Application Data

(60) Provisional application No. 63/076,207, filed on Sep. 9, 2020.

(51) Int. Cl.

| | |
|---|---|
| ***C08F 2/46*** | (2006.01) |
| ***A61L 27/18*** | (2006.01) |
| ***A61L 27/56*** | (2006.01) |
| ***A61L 27/58*** | (2006.01) |
| ***C08F 2/50*** | (2006.01) |
| ***C08G 61/04*** | (2006.01) |

(52) U.S. Cl.
CPC ............... *A61L 27/18* (2013.01); *A61L 27/56* (2013.01); *A61L 27/58* (2013.01); *A61L 2400/16* (2013.01)

(58) Field of Classification Search
CPC .......... A61L 27/56; A61L 27/16; A61L 27/18; A61L 27/58; A61L 31/146; A61L 31/148; A61L 31/048; A61L 2430/02; A61L 2430/22; A61L 2400/16; B33Y 10/00; B33Y 80/00
USPC ....... 522/165, 162, 1, 6, 189, 184, 71; 520/1
See application file for complete search history.

(56) References Cited

U.S. PATENT DOCUMENTS

| | | | |
|---|---|---|---|
| 6,849,223 | B2 | 2/2005 | Dean et al. |
| 7,702,380 | B1 | 4/2010 | Dean |
| 7,747,305 | B2 | 6/2010 | Dean et al. |
| 8,781,557 | B2 | 7/2014 | Dean et al. |
| 9,208,558 | B2 | 12/2015 | Dean et al. |
| 9,275,191 | B2 | 3/2016 | Dean et al. |
| 9,292,920 | B2 | 3/2016 | Dean et al. |
| 9,330,206 | B2 | 5/2016 | Dean et al. |
| 9,626,756 | B2 | 4/2017 | Dean et al. |
| 9,672,302 | B2 | 6/2017 | Dean et al. |
| 9,672,617 | B2 | 6/2017 | Dean et al. |
| 9,688,023 | B2 | 6/2017 | Dean et al. |
| 2011/0065616 | A1 | 3/2011 | Lourdin et al. |
| 2014/0236226 | A1 | 8/2014 | Brown et al. |
| 2016/0302911 | A1 | 10/2016 | Soletti |

FOREIGN PATENT DOCUMENTS

| | | | |
|---|---|---|---|
| WO | 2018144849 | A1 | 8/2018 |
| WO | 2019172950 | A1 | 9/2019 |
| WO | 2020014699 | A1 | 1/2020 |
| WO | 2020055816 | A1 | 3/2020 |

OTHER PUBLICATIONS

Le Fer et al, 4D Printing of Resorbable Complex Shape-Memory Poly(propylene fumarate) Star Scaffolds, Apr. 27, 2020, ACS Appl. Mater. Interfaces, 12, 22444-22452 (Year: 2020).*

J. P. Fisher, D. Dean and A. G. Mikos, Photocrosslinking characteristics and mechanical properties of diethyl fumarate/poly (propylene fumarate) biomaterials, Biomaterials, 2002, 23, 4333-4343.

Y. Luo, C. K. Dolder, J. M. Walker, R. Mishra, D. Dean and M. L. Becker, Synthesis and Biological Evaluation of Well-Defined Poly-(propylene fumarate) Oligomers and Their Use in 3D Printed Scaffolds, Biomacromolecules, 2016, 17, 690-697.

Gaëlle Le Fer and Matthew L. Becker, 4D Printing of Resorbable Complex Shape-Memory Poly(propylene fumarate) Star Scaffolds, ACS Applied Materials & Interfaces 2020 12 (20), 22444-22452.

ISR Search Report for PCT/US21/29353 dated Nov. 5, 2021.

* cited by examiner

*Primary Examiner* — Jessica Whiteley

(74) *Attorney, Agent, or Firm* — Renner, Kenner, Greive, Bobak, Taylor & Weber Co., LPA

(57) ABSTRACT

In various embodiments, the present invention is directed resorbable star PPF 4D printed structures with compressive shape memory properties. In some embodiments, these printed structures may be compressed at room temperature from a first thickness to a second thickness for insertion into the body, where they reach body temperature and expand into a desired (third) thickness. The compression and expansion of these resorbable star PPF 4D printed structures allows for easier insertion of things such as, bone scaffold and stents (e.g., vascular stents, kidney stents, urethral stents, colitis stents, esophageal stents, colon stents, intestinal stents, or venous stents) into the body, as they can be compressed prior to insertion.

42 Claims, 16 Drawing Sheets

RESORBABLE COMPLEX SHAPE MEMORY POLY(PROPYLENE FUMARATE) STAR SCAFFOLDS FOR 4D PRINTING APPLICATIONS

CROSS REFERENCE TO RELATED APPLICATIONS

This application claims the benefit of U.S. provisional patent application Ser. No. 63/076,207 entitled "Resorbable Complex Shape Memory Poly(Propylene Fumarate) Star Scaffolds For 4D Printing Applications," filed Sep. 9, 2020, and incorporated herein by reference in its entirety.

NAMES OF THE PARTIES TO A JOINT RESEARCH AGREEMENT

The present application stems from work done pursuant to a Joint Research Agreement between The University of Akron of Akron, Ohio and 3D BioActives, LLC of Akron, Ohio.

FIELD OF THE INVENTION

One or more embodiments, the present invention relates to complex shape memory scaffolds based on star-shaped poly(propylene fumarate) (PPF) copolymers. In certain embodiments, the present invention describes the 4D printing of gyroid scaffolds for use in biomedical applications from star-shaped poly(propylene fumarate) (PPF) copolymers.

BACKGROUND OF THE INVENTION

Progresses in additive manufacturing, also known as three-dimensional (3D) printing, have the full potential to revolutionize the way surgeons address complicated reconstructive efforts in many possible biomedical applications: oral, maxillofacial, and/or orthopedic trauma, cancer defect repairs, pathogenesis, congenital deformity and senescence. Efficient, reproducible, and precise methodologies for fabricating patient specific scaffolds using three-dimensional (3D) printing techniques are evolving rapidly, nevertheless, the evolution of resorbable materials is not keeping pace with the technology advances in additive manufacturing.

Soft active materials (SAMs) as a class of emerging materials with the capability of exhibiting large elastic deformation in response to environmental stimuli such as light, temperature increase, and electricity, are enabling the creation of functional active components. SAMs including shape memory polymers (SMPs), hydrogels, elastomers have been used to design "smart" materials such as biomedical devices, wearable devices or artificial muscles. However, applications of SAMs are limited by the current manufacturing approaches which constrain active structures and devices to simple geometries, often created with a single material, and they have yet to broadly exploit the potential of tailored microarchitectures.

Poly(propylene fumarate) (PPF) has been already shown remarkable properties for the construction of medical devices and 3D scaffolds for tissue engineering application using stereolithographic methods, such as cDLP (continuous digital light processing) or liquid crystal display-based printing. Indeed, its carbon-carbon double bonds can be involved in a photocrosslinking reaction to produce reliable, high-fidelity solid-cured polymer scaffolds with complex geometric designs coupled with very fine (<50 μm) features.

Nevertheless, the viscosity of linear PPF (higher than 25 Pas at 40° C.) requires, so far, a fifty percent dilution in the reactive diluent diethyl fumarate (DEF) to reduce its viscosity and make possible the 3D printing. Moreover, because the viscosity of linear PPF is closely related to its degree of polymerization, short PPF oligomers in a 0.7-3.5 kDa molar mass ($\overline{M_n}$) range are required, which limits the exploration of mechanical and degradation properties of materials resulting from the 3D printing of copolymers in a large $\overline{M_n}$ range.

To overcome this drawback, PPF-based star-shaped copolymers have been used to prepare polymeric resins with lower viscosity values, compatible with 3D printing applications, as previously reported (See, International Application Publication WO 2020/055816, the disclosure of which is incorporated herein by reference in its entirety). Multi-arm PPF copolymers were synthesized through a core-first approach using sugar-based alcohol as initiator and $Mg(BHT)_2(THF)_2$ as catalyst for controlled ring-opening copolymerization (ROCOP) of maleic anhydride (MAn) with propylene oxide (PO). The star-PPF copolymers have lower viscosities than their linear analogs, allowing the decrease of DEF ratio in resin formulation, as well as the use of higher $\overline{M_n}$. These polymers have also demonstrated shape memory properties.

What is needed in the art are resorbable star PPF 4D printed structures having shape memory properties at body temperatures that allows them to be compressed for easy insertion into the body and then expand to their operational size once inside the body.

SUMMARY OF THE INVENTION

In various embodiments, the present invention is directed a resorbable star PPF 4D printed structure having compressive shape memory properties. In one or more embodiments, these printed structures have a gyroid structure and may be compressed at room temperature from a first thickness to a second thickness for insertion into the body, where they reach body temperature and expand into a desired (third) thickness. While this behavior centers on compression and temperature-based expansion of the printed structures, the compression and expansion of these printed structures may have a profound effect on the size and shape of the printed structure before and after insertion into the body. The resorbable star PPF 4D printed structures of the present invention allow easier insertion of things such as, bone scaffold and stents (e.g., vascular stents, kidney stents, urethral stents, colitis stents, esophageal stents, colon stents, intestinal stents, or venous stents) into the body, as they can be compressed prior to insertion.

In one or more embodiments of the present invention, resorbable star PPF 4D printed structures are formed using polymeric resins based on one or more multi-arm ("star") poly(propylene fumarate) (PPF) copolymers. These resins will ordinarily also include diethyl fumarate (DEF) as a solvent and co-crosslinker to reduce the viscosity to reach a range compatible with 3D printing applications. Because the multi-arm ("star") poly(propylene fumarate) (PPF) copolymers used in the present invention will have a lower complex viscosity at a comparable number average molecular weight ($\overline{M_n}$), these resins require less DEF to arrive at a printable viscosity and have lower curing times than comparable linear PPF oligomers.

In a first aspect, the present invention is directed to a resorbable star PPF 4D printed structure having a first shape, a second compressed shape, and a third recovered shape, wherein the resorbable star PPF 4D printed structure will, when compressed from the first shape to the second compressed shape, transform to the third recovered shape over a predetermined time interval or at a predetermined temperature. In some embodiments the resorbable star PPF 4D printed structure will comprise a multi-arm PPF star polymer formed by controlled ring opening copolymerization (ROCOP) of a cyclic anhydride and an epoxide using a catalyst and a multi-functional alcohol initiator, the multi-arm PPF star polymer having a degree of polymerization of from about 40 to about 200.

In various embodiments, the resorbable star PPF 4D printed structure of the present invention includes any one or more of the above referenced embodiments of the first aspect of the present invention wherein the cyclic anhydride is at least one of maleic anhydride and succinic anhydride. In some embodiments, the epoxide is propylene oxide. In one or more embodiments, the resorbable star PPF 4D printed structure of the present invention includes any one or more of the above referenced embodiments of the first aspect of the present invention wherein multi-arm PPF star polymer formed by controlled ring opening copolymerization (ROCOP) of maleic anhydride and propylene oxide using a catalyst and a multi-functional alcohol initiator, the multi-arm PPF star polymer having a degree of polymerization of from about 40 to about 200. In some embodiments, the resorbable star PPF 4D printed structure of the present invention includes any one or more of the above referenced embodiments of the first aspect of the present invention wherein multi-arm PPF star polymer formed by controlled ring opening copolymerization (ROCOP) of succinic anhydride and propylene oxide using a catalyst and a multi-functional alcohol initiator, the multi-arm PPF star polymer having a degree of polymerization of from about 40 to about 200. In one or more embodiments, the resorbable star PPF 4D printed structure of the present invention includes any one or more of the above referenced embodiments of the first aspect of the present invention wherein multi-arm PPF star polymer has from 3 to 5 arms.

In some of these embodiments, the resorbable star PPF 4D printed structure of the present invention includes any one or more of the above referenced embodiments of the first aspect of the present invention having a glass transition temperature ($T_g$) of from about from about 10° C. to about 60° C., preferably from about 20° C. to about 50° C., and more preferably from about 30° C. to about 40° C. In one or more embodiments, the resorbable star PPF 4D printed structure of the present invention includes any one or more of the above referenced embodiments of the first aspect of the present invention having a compressive modulus of from about from about 1 MPa to about 60 MPa, preferably from about 2 MPa to about 40 MPa, and more preferably from about 3 MPa to about 25 MPa.

In some embodiments, the resorbable star PPF 4D printed structure of the present invention includes any one or more of the above referenced embodiments of the first aspect of the present invention wherein the first shape is a gyroid having a substantially uniform pore geometry and porosity. In one or more embodiments, the resorbable star PPF 4D printed structure of the present invention includes any one or more of the above referenced embodiments of the first aspect of the present invention having a plurality of struts with a strut size of from about 50 microns to about 1000 microns, preferably from about 100 microns to about 500 microns, and more preferably from about 140 microns to about 280 microns. In one or more embodiments, the resorbable star PPF 4D printed structure of the present invention includes any one or more of the above referenced embodiments of the first aspect of the present invention wherein the struts are regularly spaced. In some other embodiments, the struts are anisotropic.

In some embodiments, the resorbable star PPF 4D printed structure of the present invention includes any one or more of the above referenced embodiments of the first aspect of the present invention having a porosity of from about 15% to about 95%, preferably from about 30% to about 92%, and more preferably from about 50% to about 90%. In one or more embodiments, the resorbable star PPF 4D printed structure of the present invention includes any one or more of the above referenced embodiments of the first aspect of the present invention having a pore size of from about 50 microns to about 5000 microns, preferably from about 50 microns to about 2500 microns, and more preferably from about 50 microns to about 1000 microns.

In one or more embodiments, the resorbable star PPF 4D printed structure of the present invention includes any one or more of the above referenced embodiments of the first aspect of the present invention wherein the resorbable star PPF 4D printed structure becomes more dense under compression.

In one or more embodiments, the resorbable star PPF 4D printed structure of the present invention includes any one or more of the above referenced embodiments of the first aspect of the present invention wherein the resorbable star PPF 4D printed structure has been post-cured with UV irradiation after printing. In one or more embodiments, the resorbable star PPF 4D printed structure of the present invention includes any one or more of the above referenced embodiments of the first aspect of the present invention wherein the resorbable star PPF 4D printed structure has been post-cured for from about 1 min to about 1200 min, preferably from about 20 min to about 600 min and most preferably from about 45 min to about 90 min with UV irradiation after printing.

In one or more embodiments, the resorbable star PPF 4D printed structure of the present invention includes any one or more of the above referenced embodiments of the first aspect of the present invention wherein the predetermined time interval is from about 1 h to about 72 h at ambient temperature. In some of these embodiments, the resorbable star PPF 4D printed structure of the present invention includes any one or more of the above referenced embodiments of the first aspect of the present invention wherein the predetermined time interval is from about 1 min to about 60 min at ambient temperature.

In various embodiments, the resorbable star PPF 4D printed structure of the present invention includes any one or more of the above referenced embodiments of the first aspect of the present invention wherein the predetermined temperature is from about 20° C. to about 50° C.

In one or more embodiments, the resorbable star PPF 4D printed structure of the present invention includes any one or more of the above referenced embodiments of the first aspect of the present invention wherein the predetermined temperature is from about 20° C. to about 45° C. In some embodiments, the resorbable star PPF 4D printed structure of the present invention includes any one or more of the above referenced embodiments of the first aspect of the present invention wherein the predetermined temperature is from about 30° C. to about 42° C. In one or more embodiments, the resorbable star PPF 4D printed structure of the present invention includes any one or more of the above referenced embodiments of the first aspect of the present invention wherein the predetermined temperature is from about 30° C. to about 40° C. In some embodiments, the resorbable star PPF 4D printed structure of the present invention includes any one or more of the above referenced embodiments of the first aspect of the present invention wherein the predetermined temperature is the body temperature of a human (37° C.) or other mammal into the body of which the resorbable star PPF 4D printed structure is implanted or inserted.

In one or more embodiments, the resorbable star PPF 4D printed structure of the present invention includes any one or more of the above referenced embodiments of the first aspect of the present invention having tunable degradation and resorbability. In one or more embodiments, the resorbable star PPF 4D printed structure of the present invention includes any one or more of the above referenced embodiments of the first aspect of the present invention wherein the resorbability may be controlled by varying molar mass of the multi-arm PPF star polymer.

In one or more embodiments, the resorbable star PPF 4D printed structure of the present invention includes any one or more of the above referenced embodiments of the first aspect of the present invention wherein the first shape and the third recovered shape are the same. In one or more embodiments, the resorbable star PPF 4D printed structure of the present invention includes any one or more of the above referenced embodiments of the first aspect of the present invention wherein the third recovered shape is from about 65% and 100% of the first shape. In one or more embodiments, the resorbable star PPF 4D printed structure of the present invention includes any one or more of the above referenced embodiments of the first aspect of the present invention further comprising one or more linear PPF polymer. In one or more embodiments, the resorbable star PPF 4D printed structure of the present invention includes any one or more of the above referenced embodiments of the first aspect of the present invention comprising a bone scaffold, vascular stent, kidney stent, urethral stent, colitis stent, esophageal stent, colon stent, intestinal stent, or venous stent.

In a second aspect, the present invention is directed to a method of making the resorbable star PPF 4D printed structure described above comprising the steps of: preparing a 3D printable resin comprising a star PPF polymer; printing a 3D structure from the star PPF polymer containing 3D printable resin using a suitable 3D printer; and post-curing the 3D printed structure by UV irradiation. In some embodiments, the star PPF polymer comprises a multi-arm PPF star polymer formed by controlled ring opening copolymerization (ROCOP) of a cyclic anhydride with an epoxide using a multi-functional alcohol initiator and a catalyst and having a degree of polymerization of from about 40 to about 200. In various embodiments, the method of making the resorbable star PPF 4D printed structure of the present invention includes any one or more of the above referenced embodiments of the second aspect of the present invention wherein the cyclic anhydride is at least one of maleic anhydride and succinic anhydride and the epoxide is propylene oxide. In one or more embodiments, the method of making the resorbable star PPF 4D printed structure of the present invention includes any one or more of the above referenced embodiments of the second aspect of the present invention wherein the multi-arm PPF star polymer has from 3 to 5 PPF arms connected at a central core, the central core comprising the residue of the multi-functional alcohol initiator.

In one or more embodiments, the method of making the resorbable star PPF 4D printed structure of the present invention includes any one or more of the above referenced embodiments of the second aspect of the present invention wherein the 3D printable resin comprises a star PPF polymer having from 3 to 5 arms, diethyl fumarate (DEF), and a photoinitiator. In one or more embodiments, the method of making the resorbable star PPF 4D printed structure of the present invention includes any one or more of the above referenced embodiments of the second aspect of the present invention wherein the suitable 3D printer is a continuous digital Light processing (cDLP) 3D printer. In one or more embodiments, the method of making the resorbable star PPF 4D printed structure of the present invention includes any one or more of the above referenced embodiments of the second aspect of the present invention wherein the step of post-curing comprises irradiating the 3D printed structure with UV light for from about 1 min to about 1200 min, preferably from about 20 min to about 600 min and most preferably from about 45 min to about 90 min.

In one or more embodiments, the method of making the resorbable star PPF 4D printed structure of the present invention includes any one or more of the above referenced embodiments of the second aspect of the present invention wherein the 3D structure is a gyroid having a substantially uniform pore geometry and porosity. In one or more embodiments, the method of making the resorbable star PPF 4D printed structure of the present invention includes any one or more of the above referenced embodiments of the second aspect of the present invention wherein the 3D structure is a gyroid having a plurality of regularly placed struts with a strut size of from about 50 to about 1000, preferably from about 100 to about 500, and more preferably from about 140 to about 280. In one or more embodiments, the method of making the resorbable star PPF 4D printed structure of the present invention includes any one or more of the above referenced embodiments of the second aspect of the present invention wherein the 3D structure is a gyroid having a porosity of from about 15% to about 95%, preferably from about 30% to about 92%, and more preferably from about 50% to about 90%. In one or more embodiments, the method of making the resorbable star PPF 4D printed structure of the present invention includes any one or more of the above referenced embodiments of the second aspect of the present invention wherein the 3D structure is a gyroid having a pore size of from about 50 microns to about 5000 microns, preferably from about 50 microns to about 2500 microns, and more preferably from about 50 microns to about 1000 microns.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1A:
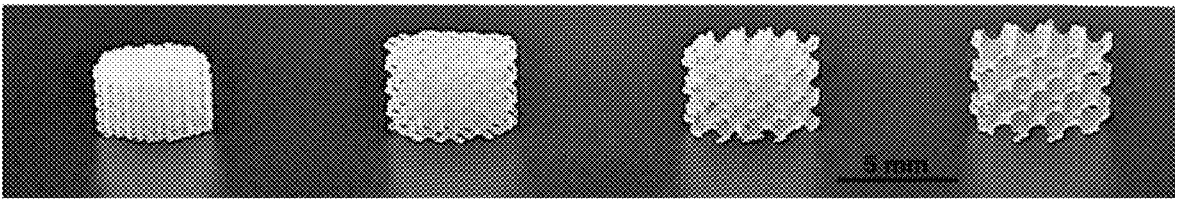
FIG. 1A is a computer-generated image comparing four gyroid scaffolds produced using a star PPF DP200 polymer with different strut sizes, from left to right: 140, 200, 240 and 280 μm.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure.

In various embodiments, the present invention is directed 3D/4D printing of PPF-based complex structures (i.e., gyroid scaffolds), able to recover their shape after compression, this property being defined herein as "shape memory behavior". In some embodiments of the present invention, the mechanical properties of the printed scaffolds can be controlled through the molar mass (or the degree of polymerization DP), the architecture of the PPF used, and the structure of the gyroid scaffolds printed. As used herein, the term "4D printing" refers to a process through which a 3D printed object transforms itself into another structure under the influence of an external energy input, such as temperature, light or other environmental stimuli.

Moreover, the scaffolds of the present invention are formed using star-shaped PPF copolymers having molar masses that are much higher than those of a linear PPF of a comparable viscosity. As a result, these polymers require significantly less solvent (generally, diethyl fumarate (DEF)) to make a 3D printable resin. This increase of the molecular mass (total DP) of the PPF used in the resin formulation leads to a significantly shorter irradiation time/layer, improved 3D printing fidelity, and better and faster shape-memory properties. In some embodiments, the scaffolds may be post-cured under UV irradiation to ensure a high crosslinking ratio, thereby improving the mechanical properties of the scaffolds.

The following terms may have meanings ascribed to them below, unless specified otherwise. As used herein, the terms "comprising" "to comprise" and the like do not exclude the presence of further elements or steps in addition to those listed in a claim. Similarly, the terms "a," "an" or "the" before an element or feature does not exclude the presence of a plurality of these elements or features, unless the context clearly dictates otherwise. Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term "about."

In the context of a polymer or copolymer, the terms "star polymer," "star-shaped," and "multi-arm" are used herein interchangeably to refer to a polymer or co polymer having 3 or more arms extending outward from a central core. As used herein, the term "arm" refers to a substantially linear polymer or copolymer chain that is bonded at one end to a central core and extends outward therefrom. As used herein, the term "3D printable," as applied to a polymer or copolymer, refers to a polymer or copolymer that can be used alone or with other ingredients such as diethyl fumarate (DEF), crosslinkers, diluents, photoinitiators, dyes, light attenuating agents, dispersants, emulsifiers, ceramics, BIOGLASS™, hydroxyapatite, β-tricalcium phosphate, and/or solvents to form a resin capable of be printed into a 3 dimensional structure using conventional additive manufacturing (3D printing) technologies. The term "residue(s)" is used herein to refer generally to the portion of a monomer or other chemical unit that has been incorporated into a polymer or other large molecule.

As will be understood by those of ordinary skill in the art, the term "degree of polymerization" (DP) generally refers to the number of number of monomer units in a macromolecule, polymer or oligomer molecule. Unless otherwise indicated herein, the degree of polymerization refers to the total number of propylene maleate, propylene succinate, or propylene fumarate units forming the resorbable multi-arm poly(propylene maleate) (PPM) star polymers, multi-arm poly(propylene maleate-co-succinate) (PPMS) star polymers, multi-arm poly(propylene fumarate) (PPF) star polymers, multi-arm poly(propylene fumarate-co-succinate) (PPFS) star polymers, linear PPF oligomers and linear PPFS oligomers described and discussed herein.

It should be also understood that the ranges provided herein are a shorthand for all of the values within the range and, further, that the individual range values presented herein can be combined to form additional non-disclosed ranges. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

All publications, patent applications, patents, and other references mentioned herein are expressly incorporated by reference in their entirety, which means that they should be read and considered by the reader as part of this text. That the document, reference, patent application, or patent cited in this text is not repeated in this text is merely for reasons of conciseness. In the case of conflict, the present disclosure, including definitions, will control. All technical and scientific terms used herein have the same meaning. Further, any compositions or methods provided herein can be combined with one or more of any of the other compositions and methods provided herein. The fact that given features, elements or components are cited in different dependent claims does not exclude that at least some of these features, elements or components maybe used in combination together.

In a first aspect, the present invention is directed to a resorbable star PPF 4D printed structure having an initial 3D printed shape, a second intermediate shape, and a third recovered shape. In one or more embodiments, a resorbable star PPF polymer resin is 3D printed as described below to form a 3D printed structure having an initial or first 3D shape. One or more forces are then applied to the initial 3D printed structure, changing its shape from its initial 3D printed shape to a second intermediate shape, which when released will transform from into a third recovered shape over a predetermined temperature and/or at a predetermined time interval.

In various embodiments, the resorbable 3D printed structures of the present invention are made from a resorbable multi-arm poly(propylene fumarate) (PPF) or poly(propylene fumarate-co-succinate) star polymer formed by controlled ring opening copolymerization (ROCOP) of a cyclic anhydride and an epoxide using a catalyst and a multi-functional alcohol initiator. The cyclic anhydride is not particularly limited, but is preferably maleic anhydride alone or with succinic anhydride. Likewise, the epoxide is not particularly limited, but is preferably propylene oxide. In some embodiments, the epoxide may be a functionalized propylene oxide monomer as described in international application publication number WO 2018/144849, the disclosure of which is incorporated herein by reference in its entirety. In these embodiments, a star polymer is initially formed by controlled ring opening copolymerization (ROCOP) of maleic anhydride and propylene oxide using a catalyst and a multi-functional alcohol initiator and will have 3 or more poly(propylene fumarate) (PPF) or poly (propylene fumarate-co-succinate) arms. The number of arms of the star polymer is determined by the number of available functional groups on the multi-functional alcohol initiator. The initial ROCOP reaction will produce a star polymer having poly(propylene maleate) (PPM) arms (usually 3-5) connected at a central core formed by the residue of the multi-functional alcohol initiator. In some embodiments, succinic anhydride may be added with the maleic anhydride to reduce the viscosity and other properties of the star polymer, in which case the initial ROCOP reaction will produce a star polymer having 3 or more poly(propylene maleate-co-succinate) (PPMS) arms.

As will be apparent to those of skill in the art, poly (propylene maleate) (PPM) is the cis isomer of poly(propylene fumarate) (PPF) and does not easily crosslink. Accordingly, the poly(propylene maleate) and poly(propylene maleate-co-succinate) star polymers are isomerized into their trans isomers to form the poly(propylene fumarate) and poly(propylene fumarate-co-succinate) (PPFS) star polymers used to make the resins for printing the resorbable 3D printed structures of the present invention. As used herein, the terms "isomerize" and "isomerization" refer broadly to the conversion of the cis-isomer (PPM) to its trans-isomer (PPF) form or, in the context of a chemical reaction or process (an "isomerization reaction") to a reaction or process that converts the cis-isomer (PPM) to its trans-isomer (PPF) form. For convenience, multi-arm star polymers with PPF and/or PPFS polymer arms will be referred to herein as "multi-arm PPF star polymers," unless otherwise indicated and it will be understood that these polymers may contain some quantity of succinate repeating units. In some embodiments, the star polymers used to form the 3D printed structures of the present invention may be those set forth in International Application Publication WO 2020/055816, the disclosure of which is incorporated herein in its entirety.

In various embodiments, the resorbable multi-arm PPF star polymer has from 3 to 5 PPF arms extending from a central core. In some embodiments, the multi-arm PPF star polymer will have 3 arms. In other embodiments, the multi-arm PPF star polymer will have 4 arms. In still other embodiments, the multi-arm PPF star polymer will have 5 arms.

In various embodiments, resorbable multi-arm PPF star polymers used to form the multi-arm 4D printed structures will have a degree of polymerization (DP) of from about 40 to about 200. In some embodiments, the resorbable multi-arm PPF star polymers will have a degree of polymerization of from about 50 to about 200, in other embodiments, from about 75 to about 200, in other embodiments, from about 100 to about 200, in other embodiments, from about 125 to about 200, in other embodiments, from about 150 to about 200, in other embodiments, from about 40 to about 175, in other embodiments, from about 40 to about 150, in other embodiments, from about 40 to about 125, in other embodiments, from about 40 to about 100, and in other embodiments, from about 40 to about 75.

In some embodiments, the resorbable 3D printed structures of the present invention may also include one or more linear PPF or PPFS oligomers to change and/or better control the cross-link density or to alter the properties of the printed polymer. In various embodiments, these linear PPF or PPFS polymer will have a DP of from about 5 to about 50. In one or more of these embodiments, the linear PPF or PPFS oligomers will comprise from about 5 wt. % to about 50 wt % of the polymer used to form the resorbable 3D printed structures of the present invention.

As set forth above, one of the advantages to the multi-arm PPF star polymers is that they have a lower complex viscosity at a comparable number average molecular weight ($\overline{M_n}$) than a comparable linear PPF polymer. The reduces the amount of reactive diluent, generally diethyl fumarate (DEF) (which acts as both solvent and crosslinking agent) needed to arrive at a printable viscosity. This is advantageous because DEF can be toxic, and the unreacted, residual, DEF must be removed from the cured scaffolds before their use, particularly if they are to be used as medical devices. These multi-arm PPF star polymers produce a resin with lower curing times than those prepared with comparable linear PPF oligomers.

In various embodiments, these multi-arm PPF star polymers will have glass transition temperature ($T_g$) values of from about −20° C. and about 40° C., as measured by using differential scanning calorimetry (DSC). In some embodiments, the multi-arm PPF star polymers will have glass transition temperature ($T_g$) of from about −10° C. and about 40° C., in other embodiments, from about 0° C. to about 40° C., in other embodiments, from about 10° C. to about 40° C., in other embodiments, from about 20° C. to about 40° C., in other embodiments, from about 30° C. to about 40° C., in other embodiments, from about −20° C. to about 30° C., in other embodiments, from about −20° C. to about 20° C., in other embodiments, from about −20° C. to about 10° C., in other embodiments, from about −20° C. to about 0° C., and in other embodiments, from about −20° C. to about −10° C., as measured by using differential scanning calorimetry (DSC). In some embodiments, the multi-arm PPF star polymers will have a $T_g$ of from about −2° C. and about 10° C., as measured by using differential scanning calorimetry (DSC).

Further, unlike linear PPF oligomers for which $T_g$ values have been found to increase with increases in the $\overline{M_n}$, the multi-arm star PPF star polymers showed a decrease in $T_g$ values as the $\overline{M_n}$ increases. Because of this, polymer structures produce with a target $T_g$ (e.g., human body temperature), will have a higher $\overline{M_n}$ and with it a improved 3D printing fidelity, better and faster shape-memory properties, and better mechanical properties than corresponding structures made with corresponding linear PPF oligomers.

The initial 3D printed shape of the resorbable star PPF 4D printed structure is not particularly limited and may be any 3D printable shape. As will be apparent to those of skill in the art, the initial 3D printed shape of the resorbable star PPF 4D printed structures may be designed using conventional Computer Aided Design (CAD) software and printed on any suitable 3D printer. In some embodiments, the resorbable star PPF 4D printed structures may be designed using MATLAB™ software (The MathWorks, Inc., Natick, MA). In one or more embodiments, the initial 3D printed shape may be printed using stereolithographic methods, such as cDLP (continuous digital light processing) or liquid crystal display-based printing. In one or more embodiments, the initial shape of the resorbable star PPF 4D printed structures may be that of a bone scaffold, a vascular stent, a kidney stent, a urethral stent, a colitis stent, an esophageal stent, a colon stent, an intestinal stent, or a venous stent.

In some embodiments, the initial 3D printed shape of the resorbable star PPF 4D printed structure is a gyroid shape having a substantially uniform pore geometry and porosity. In some embodiments, the initial 3D printed shape will be a gyroid structure having a Schoen gyroid triply periodic minimal surface having a plurality of struts and a plurality of pores. (See, FIGS. 1A, 2A-C, 3A-C, 4A-C, 5A-C and 9B) Because the internal pore geometry directly impacts the capacity of a scaffold to guide neo-tissues, the vasculature infusion into a defect can improve cell seeding and/or nutrient flow for ex vivo culturing. In some of these embodiments, the struts are all regularly spaced throughout the structure. In some other embodiments, the struts are anisotropic.

In these embodiments, the initial 3D printed shape will be a gyroid structure having a plurality of struts with a strut size of from about 50 microns to about 1000 microns, preferably from about 100 microns to about 500 microns, and more preferably from about 140 microns to about 280 microns. In some of these embodiments, the initial 3D printed shape will be a gyroid structure having a porosity of from about 15% to about 95%, preferably from about 30% to about 92%, and more preferably from about 50% to about 90%. In some of these embodiments, the initial 3D printed shape will be a gyroid structure having a pore size of from about 50 microns to about 5000 microns, preferably from about 50 microns to about 2500 microns, and more preferably from about 50 microns to about 1000 microns.

As set forth above, the initial 3D printed shape of the resorbable star PPF 4D printed structures of the present invention also has a corresponding compressed shape having a compressed volume that is less than the volume of the initial 3D printed shape. In one or more embodiments, the corresponding compressed shape will have a compressed volume that is from about 5% to about 90% less than the volume of the initial 3D printed shape. In some other embodiments, the second shape may have a comparable volume, but a different shape. In some embodiments, the second or compressed shape will have a volume that is from about 5% to about 80%, in other embodiments, from 10% to 90%, in other embodiments, from 20% to 90%, in other embodiments, from 30% to 90%, in other embodiments, from 40% to 90%, in other embodiments, from 60% to 90%, in other embodiments, from 75% to 90%, in other embodiments, from 5% to 70%, in other embodiments, from 5% to 50%, in other embodiments, from 5% to 40%, in other embodiments, from 5% to 30%, and in other embodiments, from 5% to 20%, less than the volume of the initial 3D printed shape.

In some embodiments, the resorbable 3D printed star PPF structure of the present invention will change from its compressed shape to its recovered shape over a time interval of from about 5 min to about 72 h, in other embodiments, from about 30 min to about 72 hours, in other embodiments, from about 1 hour to about 72 hours, in other embodiments, from about 10 hours to about 72 hours, in other embodiments, from about 30 hours to about 72 hours, in other embodiments, from about 50 hours to about 72 hours, in other embodiments, from about 1 min to about 60 hours, in other embodiments, from about 1 min to about 50 hours, in other embodiments, from about 1 min to about 30 hours, in other embodiments, from about 1 min to about 15 hours, and in other embodiments, from about 1 min to about 5 hours at ambient temperature.

The type and amount of force that may be applied to change the initial 3D printed shape into the second intermediate shape is not particularly limited, but should not be so much as to crush or otherwise permanently damage the structure. In some embodiments, the force applied may be a compressive force. In some other embodiments, the force applied may be a rotational or twisting force. In still other embodiments, the force applied may be an elongation or bending force.

In one or more embodiments, the resorbable star PPF 4D printed structures of becomes more dense under compression. As a result, they will have a smaller external area and can be inserted more easily into the body.

Finally, when the compressive force is released, the compressed shape will transform into a third or recovered shape over time and/or under the influence of an external energy input, such as temperature, light or other environmental stimuli. In some other embodiments, the resorbable 4D printed star PPF structure of the present invention will change from its compressed shape to its recovered shape at a predetermined temperature. The recovery temperature will depend upon a variety of factors including, but not limited to, the $T_g$ of the resorbable 4D printed star PPF structure, and the presence and degree of hydrogen bonding within the structure. In some embodiments, the predetermined temperature triggering shape recovery is from about 20° C. to about 50° C., in other embodiments, from about 20° C. to about 45° C., in other embodiments, 30° C. to about 42° C., and in other embodiments, 30° C. to about 40° C. In various embodiments, the predetermined temperature triggering recovery is the body temperature of a human (37° C.) or that the mammal into the body of which said resorbable star PPF 4D printed structure is to be implanted or inserted.

In one or more embodiments, the compressed shape will transform into a third or recovered shape at the end of a predetermined time interval or at a predetermined temperature. In some embodiments, the initial printed shape and the third recovered shape are the same and the resorbable star PPF 4D printed structure will return to its initial shape over a predetermined time interval or at a predetermined temperature. However, this need not be, and is generally not, the case. In various embodiments, the recovered shape will be from about 65% to about 100% of the volume of the initial printed structure. In some embodiments, the recovered shape will be from about 70% to about 100%, in other embodiments, from about 77% to about 100%, in other embodiments, from about 80% to about 100%, in other embodiments, from about 85% to about 100%, in other embodiments, from about 80% to about 100%, in other embodiments, from about 95% to about 100%, in other embodiments, from about 65% to about 95%, in other embodiments, from about 65% to about 90%, in other embodiments, from about 65% to about 85%, in other embodiments, from about 65% to about 80%, and in other embodiments, from about 65% to about 75%, of the volume of the initial printed structure.

As set forth above, in some embodiments, the resorbable 3D printed star PPF structure of the present invention will change from its compressed shape to its recovered shape over a predetermined time interval. In one or more of these embodiments, the resorbable 3D printed star PPF structure of the present invention will change from its compressed shape to its recovered shape over a time interval of from about 1 min to about 72 h at ambient temperature. In some embodiments, the resorbable 3D printed star PPF structure of the present invention will change from its compressed shape to its recovered shape over a time interval of from about 5 min to about 72 h, in other embodiments, from about 30 min to about 72 hours, in other embodiments, from about 1 hour to about 72 hours, in other embodiments, from about 10 hours to about 72 hours, in other embodiments, from about 30 hours to about 72 hours, in other embodiments, from about 50 hours to about 72 hours, in other embodiments, from about 1 min to about 60 hours, in other embodiments, from about 1 min to about 50 hours, in other embodiments, from about 1 min to about 30 hours, in other embodiments, from about 1 min to about 15 hours, and in other embodiments, from about 1 min to about 5 hours at ambient temperature. In some embodiments, the resorbable 3D printed star PPF structure of the present invention will change from its compressed shape to its recovered shape over a time interval of from about 1 hour to about 72 h at ambient temperature. In some other embodiments, the resorbable 3D printed star PPF structure of the present invention will change from its compressed shape to its recovered shape over a time interval of from about 1 min to about 60 min at ambient temperature.

In one or more embodiments, the resorbable star PPF 4D printed structures will have a glass transition temperature ($T_g$) of from about from about 10° C. to about 60° C. as measured by differential scanning calorimetry (DSC). In some of these embodiments, the resorbable star PPF 4D printed structures will have a $T_g$ of from about from about 15° C. to about 60° C., in other embodiments, from about 20° C. to about 60° C., in other embodiments, from about 30° C. to about 60° C., in other embodiments, from about 40° C. to about 60° C., in other embodiments, from about 50° C. to about 60° C., in other embodiments, from about 10° C. to about 50° C., in other embodiments, from about 10° C. to about 45° C., in other embodiments, from about 10° C. to about 40° C., in other embodiments, from about 10° C. to about 25° C., in other embodiments, from about 10° C. to about 20° C., and in other embodiments, from about 10° C. to about 15° C. as measured by differential scanning calorimetry (DSC). In some embodiments, the $T_g$ of the resorbable star PPF 4D printed structures will be from about 20° C. to about 50° C. In some other embodiments, the $T_g$ of the resorbable star PPF 4D printed structures will be from about 30° C. to about 40° C., as measured by differential scanning calorimetry (DSC).

It was found that different post-curing times (i.e., 45 min or 90 min) under UV irradiation, leads to different macroscopic properties. It was generally observed that the $T_g$ of the resorbable star PPF 4D printed structure increases when the post-curing time increases, indicating lower chain mobility due to a higher crosslinking ratio. In other embodiments, it was found that a strut size increase induces a $T_g$ decrease, indicating a lower crosslinking ratio, due to the lower penetration of UV light into the larger sized strut.

In various embodiments of the resorbable star PPF 4D printed structures of the present invention, the compressive modulus varied between about 1 MPa and 60 MPa as measured by Instron tensile tester. In some embodiments, the compressive modulus of the resorbable star PPF 4D printed structures will be about 1 and 60 MPa, in other embodiments, from about 2 MPa to about 60 MPa, in other embodiments, from about 10 MPa to about 60 MPa, in other embodiments, from about 20 MPa to about 60 MPa, in other embodiments, from about 30 MPa to about 60 MPa, in other embodiments, from about 40 MPa to about 60 MPa, in other embodiments, from about 1 MPa to about 50 MPa, in other embodiments, from about 1 MPa to about 40 MPa, in other embodiments, from about 1 MPa to about 30 MPa, in other embodiments, from about 1 MPa to about 20 MPa. In some embodiments, the compressive modulus of the resorbable star PPF 4D printed structures will be from about 2 MPa and 40 MPa. In some other embodiments, the compressive modulus of the resorbable star PPF 4D printed structures will be from about 3 and 25 MPa. In some of these embodiments, the compressive modulus was generally found to be the greatest after a longer post-cure treatment. In some of these embodiments, it was found that a longer post-curing time can increase the compression modulus while making the scaffolds more brittle.

As set forth above, the star PPF 4D printed structures of the present invention allow tunable degradation and resorbability. In various embodiments, the resorbability of the resorbable star PPF 4D printed structures can be tuned depending on the molar mass (or the degree of polymerization DP), the architecture of the multi-arm PPF star polymer used, and the structure of the gyroid scaffolds. As will be apparent, as the DP (molar mass) of the multi-arm PPF star increases, the degradation and resorbability rate will likewise increase. The opposite is also true; the degradation and resorbability rate will descrease with a decrease in the DP of the multi-arm PPF star polymer being used. The degradation/resorbability rate will also vary with the surface area of the resorbable star PPF 4D printed structure printed. Finally, the degradation rate may also be controlled through the architecture of the multi-arm PPF star polymer used.

In a second aspect, the present invention is directed to a method of making the resorbable star PPF 4D printed structure described above. In various embodiments, the method comprises the steps of: (1) preparing a 3D printable resin comprising a multi-arm star PPF polymer; (2) printing a 3D structure from the 3D printable resin using a suitable 3D printer; and (3) post-curing the 3D printed structure by UV irradiation to produce the resorbable star PPF 4D printed structure of the present invention.

In one or more embodiments, the 3D printable resin comprises one or more of the resorbable multi-arm star PPF polymers described above, a quantity of diethyl fumarate (DEF) sufficient to obtain a 3D-printable viscosity, and a photoinitiator. The viscosity of the 3D printable resin will generally depend upon the requirements of the particular 3D printer being used. In various embodiments, the 3D-printable resin will have a complex viscosity of from about 0.25 Pas to about 15 Pas.

As will be apparent, the DEF serves both as a solvent/diluent for the resorbable multi-arm PPF star polymers and as a crosslinking agent when the polymer is later printed and cured. In various embodiments, the 3D printable resin will comprise from about 50 wt % to about 70 wt % of the resorbable multi-arm PPF star polymers described above. In some embodiments, the 3D printable resin of the present invention will comprise from about 55 wt % to about 70%, in other embodiments, from about 60 wt % to about 70 wt. %, in other embodiments, from about 65 wt. % to about 70 wt. %, in other embodiments, from about 50 wt % to about 65 wt. %, in other embodiments, from about 50 wt. % to about 60 wt. %, and in other embodiments, from about 50 wt % to about 55 wt % of the resorbable multi-arm PPF star polymers described above.

As set forth above, the 3D printable resin may in some embodiments also comprise one or more linear PPF or linear PPFS oligomers having a DP of from about 5 to about 50 In some embodiments, the 3D printable resin will comprise from about 2.5 wt. % to about 40 wt. % of these linear PPF and/or linear PPFS oligomers.

The 3D printable resin will also contain one or more photoinitiators. The photoinitiators that may be used in the 3D printable resin are not particularly limited and any photoinitiator capable of producing a radical at a suitable wavelength (approximately 254-450 nm) may be used. As will be appreciated by those of skill in the art, the choice of photoinitiator is often dictated by the requirements of the 3D printer being used. Suitable photoinitiators may include, without limitation, phenylbis(2,4,6-trimethylbenzoyl)phosphine oxide (BAPO), IRGACURE™ 819/BAPO (BASF, Florham Park, NJ) or IRGACURE™ 784 (BASF, Florham Park, NJ).

In addition, the 3D printable resin may contain one or more other additives commonly used in 3D printable resins such as dyes, light attenuating agents, radical scavengers, dispersants, emulsifiers, ceramics, bioglass, hydroxyapatite, β-tricalcium phosphate, crosslinkers and/or solvents. The dyes that may be used are not particularly limited and may be any dye conventionally used in 3D printing, provided they do not quench the radicals necessary for crosslinking. The light attenuating agents that may be used are likewise not particularly limited and may include, without limitation, oxybenzone (2-Hydroxy-4-methoxybenzophenone) (Sigma-Aldrich). Suitable emulsifiers may include, without limitation, sucrose, threhalose, or any sugar molecule.

In various embodiments, the 3D printable resin may also include one or more other additives to support and/or promote tissue growth. The additives are not particularly limited provided they do not quench the radicals needed for crosslinking of the 3D printable resin. In various embodiments, the 3D printable resin may contain additives such as, ceramics, SIOGLASS™, hydroxyapatite, β-tricalcium phosphate, and combinations thereof.

In some other embodiments of the present invention, the 3D printable resin used to make the resorbable star PPF 4D printed structures of the present invention may itself be a mixture of 3D printable resins having resorbable multi-arm star PPF polymers with various number of arms, various ratios of linear PPF and various ratios of reactive solvent DEF.

In one or more embodiments, the 3D printable resin may be formed by dissolving one or more of the resorbable multi-arm PPF star polymers described above in from about 30 wt. % to about 50 wt. % DEF to form a PPF:DEF solution containing from about 50 wt. % to about 70 wt. % of the resorbable multi-arm PPF star polymers described above. The various other resin components described above (e.g. photoinitiators, dyes, light attenuating agents, dispersants, emulsifiers, ceramics, bioglass, hydroxyapatite, β-tricalcium phosphate, crosslinkers and/or solvents) may be added to the 3D printable resin at any time prior to the crosslinking of the PPF polymer and are mixed evenly throughout the resin, as is known in the art. In some of these embodiments, a PPF/DEF solution having from about 50 wt. % to about 70 wt. % of the resorbable multi-arm PPF star polymers described above is first prepared. Next, two photoinitiators, phenylbis(2,4,6-trimethylbenzoyl)phosphine oxide (SAPO) and Irgacure 784, and a radical scavenger oxybenzone (HMS) are added to the PPF:DEF solutions at 3%, 0.4% and 0.7% by weight, respectively and mixed evenly throughout the resin, following a previously reported protocol with modification in the mixing ratio of copolymer and DEF to obtain a 3D printable star PPF resin. See, J. P. Fisher, D. Dean and A. G. Mikos, Biomaterials, 2002, 23, 4333-4343 and Y. Luo, C. K. Dolder, J. M. Walker, R. Mishra, D. Dean and M. L. Becker, *Biomacromolecules,* 2016, 17, 690-697, the disclosures of which are incorporated herein in their entirety.

The 3D printable resins described above may be printed using conventional additive manufacturing (3D printing) techniques, such as stereolithography or continuous digital light processing (cDLP) techniques and photocrosslinked to form 3D printed structures having virtually any shape. Any suitable light-based 3D printer may be used. Suitable 3D printers may include, without limitation, Carbon3D printers (CARBON3D™, Redwood City, CA), PERFACTORY™ P3 3D printer (EnvisionTEC, Dearborn, MI), Micro HR 279 printer EnvisionTEC (Dearborn, MI, USA), photocentric stereolithographic or photochemical 3D printers. In some embodiments, the 3D printable resins described above may be printed using a Micro HR 279 (EnvisionTEC, Dearborn, MI, USA) printer using a 405 nm LED UV light projector with an irradiance of 225 $mW \cdot dm^{-2}$.

In various embodiments, the resorbable star PPF 4D printed structure may be formed by first generating a set of instructions for 3D printing a desired structure and sending those instructions to a suitable 3D printer. In some of these embodiments, the set of instructions may comprise a computer assisted design (CAD) file generated using suitable computer software that are readable by the 3D printer to be used. In some embodiments, the design files may be created using SolidWorks software (Dassault Systems SolidWorks Corp., Waltham, MA). In some embodiments, the CAD models were sliced digitally into layers using the Perfactory software suite prior to manufacturing. The Perfactory P3 is an inverted system that projects upward through a transparent glass plate into a reservoir containing the resin. In one or more embodiments, the CAD or other computer file containing instructions for printing the star PPF printed structure may be generated as set forth in U.S. Pat. Nos. 6,849,223, 7,702,380, 7,747,305, 8,781,557, 9,208,558, 9,275,191, 9,292,920, 9,330,206, 9,626,756, 9,672,302, 9,672,617, and 9,688,023, the disclosures of which are incorporated herein by reference in their entirety.

Additive manufacturing, especially digital light processing (DLP), allows for the design and printing of arbitrarily shaped objects. Thus, in some embodiments, anatomically shaped implants designed directly from patient computed tomography-data can be fabricated. In other embodiments, resorbable star PPF 4D printed structure may be printed from CAD files describing a gyroid structures as shown in FIGS. 1A, 2A-C, 3A-C, 4A-C, 5A-C and 9B and discussed herein.

In various embodiments, the resorbable star PPF 4D printed structures may be printed slightly larger than their desired size to account for shrinkage. In some of these embodiments, for various PPF, the shrinkage phenomenon induces lower values than expected both in diameter and in height, moreover, lower the strut size, higher this discrepancy. While not wishing to be bound by theory, a possible reason for this is that low strut sizes facilitate the photo-crosslinking, and consequently the shrinkage, by reducing the chain-to-chain distance. Due to the reproducibility of this shrinkage, however, it is believed that the minor disparities between the CAD models and the structures obtained, it is possible to predict and compensate for the disparity.

In some embodiments, the scaffolds may be post-cured under UV irradiation for a post-curing time of from about 1 min to 1200 min. This step ensures a higher crosslinking ratio and consequently improves the mechanical properties. In some embodiments, the scaffolds may be post-cured for from about 5 min to about 1200 min, in other embodiments, from 30 min to 1200 min, in other embodiments, from 90 min to 1200 min, in other embodiments, from 200 min to 1200 min, in other embodiments, from 500 min to 1200 min, in other embodiments, from 800 min to 1200 min, in other embodiments, from 1 min to 900 min, in other embodiments, from 1 min to 600 min, in other embodiments, from 1 min to 300 min, and in other embodiments, from 1 min to 150 min. In some other embodiments, the scaffolds may be post-cured for from about 20 min to about 600 min. In still other embodiments, the scaffolds may be post-cured for from about 45 min to about 90 min.

Moreover, the post-curing time has been shown to influence both of the post-curing step duration and the temperature on the shape-memory properties. Indeed, generally, it has been found that the lower the post-curing time, the lower the temperature allowing the recovery. Similarly, it has been found that the higher the post-curing time, the higher the temperature allowing the recovery. In addition, it has also been found that a longer post-curing time can increase the compression modulus while making the scaffolds more brittle.

EXPERIMENTAL

In order to illustrate and further reduce the present invention to practice, series of gyroid shaped resorbable star PPF 4D printed structures according to the present invention were printed and evaluated. The following examples are offered to more fully illustrate the invention but are not to be construed as limiting the scope thereof. Further, while some of examples may include conclusions about the way the invention may function, the inventors do not intend to be bound by those conclusions but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is number average molecular weight, temperature is in degrees Centigrade, viscosity is in Pas, and pressure is at or near atmospheric.

Materials

All reagents were purchased from Sigma-Aldrich (St. Louis, MO, USA). All solvents were purchased from Fisher Scientific (Hampton, NH, USA) and dried using an Innovative Technology Inc. (Newburyport, MA, USA) Pure Solv MD-3 solvent purification system. $Mg(BHT)_2(THF)_2$ was synthesized as reported previously. (See, International Application Publication WO 2019/172950, the disclosure of which is incorporated herein in its entirety). Meso-erythritol was dried by azeotropic distillation before use. Maleic anhydride was dried under vacuum over $P_2O_5$ for one week. Propylene oxide was dried over calcium hydride overnight prior to vacuum distillation. All other reagents were used as received.

Methods

The scaffolds were imaged using an Olympus Stereoscope (Center Valley, PA, USA) to depict the gyroid architecture features in greater detail. The structure of the gyroid scaffolds were characterized nondestructively using X-ray micro-computed tomography (μ-CT) Skyscan 1172 (Bruker; Billerica, MA, USA). 3D scanning of scaffolds was carried out using the following parameters: 40 kV voltage, medium camera (pixel size=8.73 μm), no filter, 238 ms camera exposure preset time and 7.0 μm resolution. Differential scanning calorimetry (DSC) was performed using a DSC-TA Discovery DSC250 (New Castle, DE, USA) scanning a temperature range from −40 to 80° C. with heating and cooling ramps of 10° C.·min$^{-1}$. The glass transition temperature ($T_g$) was determined from the midpoint of the transition in the second heating cycle. The mechanical properties of the gyroid scaffolds were studied by compression tests using an Instron 5566 Universal Testing Machine (Norwood, MA, USA). Force and displacement were zeroed prior to compression, with the top plate slightly above the surface of the sample. Samples were compressed at a constant crosshead velocity of 0.5 mm·min$^{-1}$ at room temperature while stress and strain were monitored throughout the experiment. Compression was stopped at 80% strain. The compressive moduli were calculated using the slope of linear fitting in the first linear regime. The reported results are average values from five individual measurements and the associated errors are the standard deviations.

The recovery of the scaffolds after compression was first evaluated my measuring their thickness overtime with a digital calliper at room temperature and at 40° C. and plotting the actual height/initial height ratio versus time. Each point is a duplicate and the associated error bars are equal to the standard deviations. Degradation was assessed in an accelerated in vitro environment to highlight how the chemistry and printing design modulate it. The purpose of the accelerated conditions was not to determine the necessary time which to degrade the samples in vivo, but first to demonstrate the resorbability and to explicate the relationships between scaffold properties and degradation kinetics. Degradation was evaluated over 40 days in a sodium hydroxide solution (0.1 M NaOH, pH=13) under stirring at 50 rpm. Scaffolds were submerged in 4 mL of solution in individual glass vials, capped, and maintained at 37° C. Throughout the study, the NaOH solution was replaced with fresh solution every second day. At each time point (days 0, 4, 8, 15, 20, 40), three samples were removed for analysis and washed in deionized water for 2 min. The scaffolds were dried in an oven at 37° C. for 24 h. The mass of each scaffold was determined prior to the experiment and again at their respective time points after drying using a high precision electronic balance, three measurements were made, and the average was recorded. The percent mass loss was calculated for each sample as follows:

$$\%\text{ mass loss} = 100 - \frac{m_t \times 100}{m_0} \quad \text{Equation 1}$$

where $m_0$ is the initial mass and $m_t$ is the mass at the instant t. The scaffolds were then observed by optical microscopy using an Olympus Stereoscope (Center Valley, PA, USA).

Procedures

Synthesis of star-shaped poly(propylene maleate) (PPM). Four-arm star-shaped poly(propylene maleate) (PPM) copolymers were synthesized as previously reported (polymer chemistry) by ring-opening copolymerization (ROCOP) of maleic anhydride (MAn) and propylene oxide (PO) using meso-erythritol as initiator. Various [monomers]/[initiator] molar ratios were used to obtain copolymers with different PPM arm lengths and consequently various total degrees of polymerization (DPs). For instance, four-arm star PPM with target total degree of polymerization (DP) 40, was prepared as follows: in a glovebox, meso-erythritol (112.12 g·mol$^{-1}$, 124.5 mg, 1.02 mmol), $Mg(BHT)_2(THF)_2$ (604.95 g·mol$^{-1}$, 123.4 mg, 2.04×10$^{-1}$ mmol), anhydrous toluene (10.2 mL), MAn (98.06 g·mol$^{-1}$, 4.0 g, 40.8 mmol) and PO (58.08 g·mol$^{-1}$, 2.85 mL, 40.8 mmol) were introduced, in this order, in a flame-dried Schlenk tube. The Schlenk tube was sealed with PTFE plug and removed from the glovebox. The solution was stirred at 80° C. for 48 h (typically until the PPM precipitates in the bottom of the Schlenk and the supernatant looked clear). The resultant copolymer was recovered by precipitation in diethyl ether and then dried under vacuum to afford a highly viscous oil. Yield: 78%.

Isomerization of PPM. Copolymer was dissolved in chloroform at a concentration of 0.5 mol·L$^{-1}$ of MAn residues and diethylamine (DEA) was added to reach 0.15 eq/MAn residue. As an example, four-arm star PPM with target total DP40 were isomerized in the corresponding four-arm star PPF as follows: star-shaped PPM (4.8 g, 7.62×10$^{-1}$ mmol, 30.5 mmol of olefin) was dissolved into chloroform (61 mL, 0.5 mol·L$^{-1}$ of olefin), DEA (0.47 mL, 0.15 mol. eq. olefin) was added and the solution was heated under reflux for 24 h under a nitrogen atmosphere. After cooling to room temperature, the organic solution was washed with 1 M sodium phosphate solution (250 mL, pH=6) and the copolymer was recovered after evaporation of the chloroform. Yield: 95%.

Resin preparation. Polymeric resins were prepared by mixing star-shaped PPF with reactive diluent diethyl fumarate (DEF), which acts as both solvent and crosslinking agent. Various PPF:DEF weigh ratios were investigated, i.e., 70:30, 60:40 and 50:50 wt %. PPF and DEF were carefully introduced in the flask and mixtures were maintained at 45° C. overnight under stirring to insure a good mixing. In order to print 3D scaffolds, two photoinitiators, phenylbis(2,4,6-trimethylbenzoyl)phosphine oxide (SAPO) and Irgacure 784, and a radical scavenger oxybenzone (HMS) were added to the PPF:DEF solutions at 3%, 0.4% and 0.7% by weight, respectively. and mixed evenly throughout the resin, following a previously reported protocole.[3,4]

Gyroid scaffold design. Each scaffold was cylindrical with a prescribed diameter of 6 mm and height of 4 mm. Schoen's gyroid triply periodic minimal surface was used as the geometric foundation for the pore architecture allowing full control over the porosity, and the pore and strut sizes. In this work, four different architectures were investigated with constant pore geometry and porosity (88.2%) but varying the strut size from 140 to 280 μm and consequently the pore size from 489 to 978 μm. The gyroid parameters and the dimensions are given in Table 1, below.

TABLE 1

Pore design parameters of gyroid scaffolds.

| Architecture | Porosity (%) | Strut size (μm) | Pore size (μm) |
|---|---|---|---|
| CAD model 1 | 88.2 | 140 | 489 |
| CAD model 2 | 88.2 | 200 | 699 |
| CAD model 3 | 88.2 | 240 | 838 |
| CAD model 4 | 88.2 | 280 | 978 |

Although cylindrical structures were used in this work, additive manufacturing, especially digital light processing (DLP), allows this same design methodology to be applied to arbitrarily shaped objects. Thus, anatomically shaped implants designed directly from patient computed tomography-data can be fabricated.

3D printing of gyroid scaffolds. Gyroid scaffolds were printed from liquid resins with an EnvisionTEC (Dearborn, MI, USA) Micro HR 279 printer using a 405 nm LED UV light projector with an irradiance of 225 $mW \cdot dm^{-2}$ and the computer-aided design (CAD) models were digitally sliced into layers using the Perfactory software suite prior to manufacturing. The Perfactory P3 is an inverted system that projects upward through a transparent glass plate into a reservoir containing the resin. After each projection, the build platform moves vertically upward to allow resin inflow for the next layer. Prior to scaffold printing, cure tests of PPF-based resins were performed to determine the optimal printed layer thickness and UV exposure time depending on the resin formulation. 20 mg of resin were placed in the middle of the resin tray and after irradiation with UV for varying time durations (i.e., 60, 120, 180 and 240 s), the uncured liquid resin was gently removed by tissue paper. The resulting film was peeled off the resin tray with a razor blade and the thickness of the cured film was measured by a digital calliper (Marathon, Vaughan, Ontario, Canada) with 10 μm precision. Following these cure tests and printing tests, the layer thickness was fixed to 25 μm and projection time ranged from 60 s to 225 s depending on the PPF molar mass. After printing, scaffolds were immediately rinsed with acetone, 70% ethanol (v/v), and distilled water for 15 s each. Finally, the "green" scaffolds were post-cured in a full spectrum UV irradiation chamber for 45 min or 90 min. The scaffold diameters and heights were measured with a digital caliper to quantify the shrinkage.

Example 1

3D/4D Printing of Gyroid Scaffolds Based on Linear PPF DP10 and PPF Stars DP40 and DP200

PPF:DEF (50:50) resins based on the four-arm star PPF DP40 and DP200 were used for digital light processing (DLP) 3D printing of gyroid scaffolds, after addition of photo-initiators and radical scavenger. Linear DP10 PPF oligomer resin (50:50) was also used for comparison. Cure tests and printing tests were performed to determine the most appropriate UV exposure time/layer for each formulation. A 25 μm layer thickness allowed for a better attachment of the gyroid structures on the basement plate while an increase of the total DP of the PPF used in the formulation led to a significant decrease of the curing time/layer. Indeed, for the linear PPF DP10, a curing time/layer of 225 s was necessary, when only 95 s and 60 s allowed the printing for the star PPF DP40 and DP200 respectively. Consequently, the total printing duration of scaffolds with a 4 mm height has been reduced from more than 13 h for the linear DP10 to less than 5 h30 for the star DP200.

Porous, cylindrical scaffold were printed using CAD files describing gyroid structures with four different architectures, constant pore geometry and porosity (88.2%) but varying the strut size (140, 200, 240 and 280 μm) and consequently the pore size (respectively 489; 699, 838 and 978 μm) (FIG. 1A). After printing, uncrosslinked PPF:DEF solution was removed from the scaffolds and the scaffold were post-cured under UV irradiation for 45 min or 90 min. This step is necessary to ensure a higher crosslinking ratio and consequently improve the mechanical properties, but the effects of its duration were not previously investigated.

Example 2

Characterization of Gyroids Scaffolds Based on Linear PPF DP10 and PPF Stars DP40 and DP200

Figure 1B:
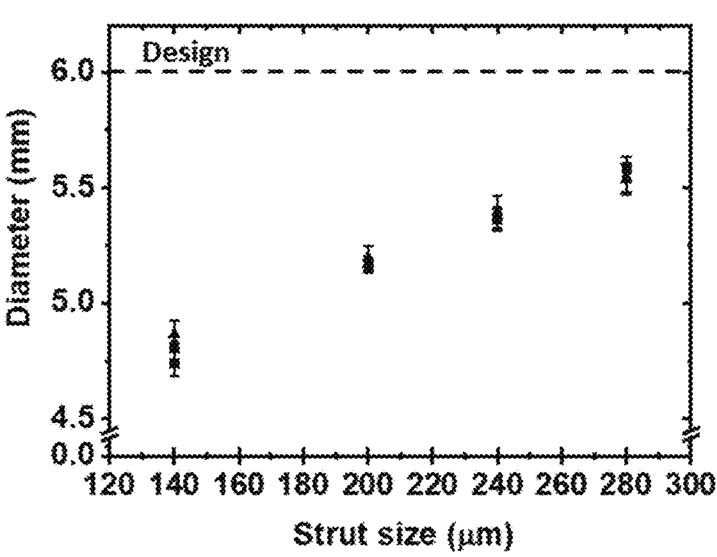
FIGS. 1B-C are graphs showing the variation of diameter (FIG. 1B) and height (FIG. 1C) of 3D printed scaffolds as a function of their strut size and the PPF used.
Figure 1C:
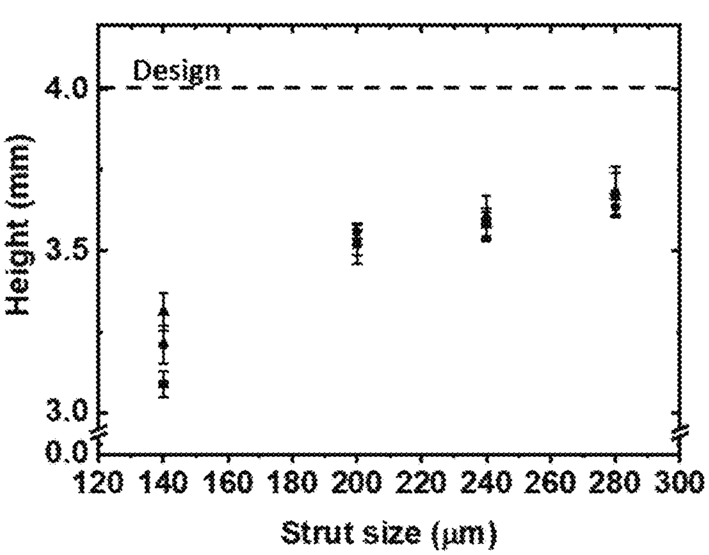
Figure 2A:
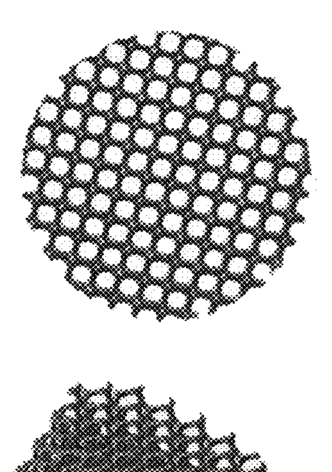
FIG. 2A is a computer-generated image showing a top view (upper) and a perspective view (lower) of a structure having a Schoen gyroid triply periodic minimal surface with 140 μm strut size, 489 μm pore size, and 88.2% porosity generated from a CAD file created using MATLAB™ software (The MathWorks, Inc., Natick, MA) (CAD model 1).
Figure 2A:
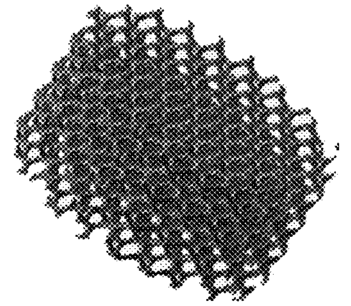
Figure 2B:
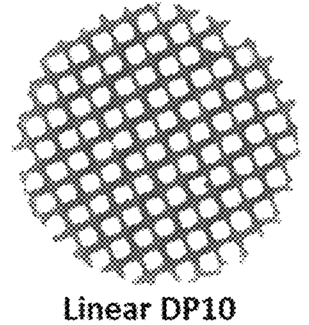
FIG. 2B is a comparison of optical micrographs showing a top view of scaffolds obtained by 3D printing the structure shown in FIG. 2A above, using three different PPF polymers (from left to right: linear PPF DP10, star PPF DP40, star PPF DP200).
Figure 2B:
Figure 2B:
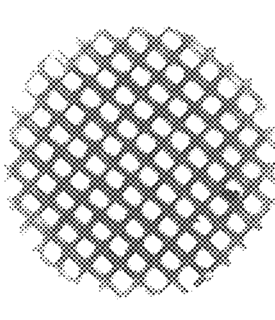
Figure 2B:
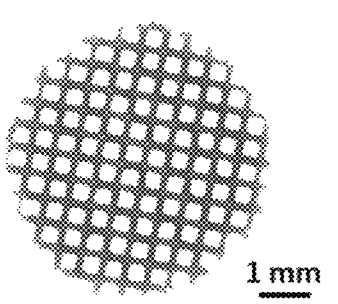
Figure 2C:
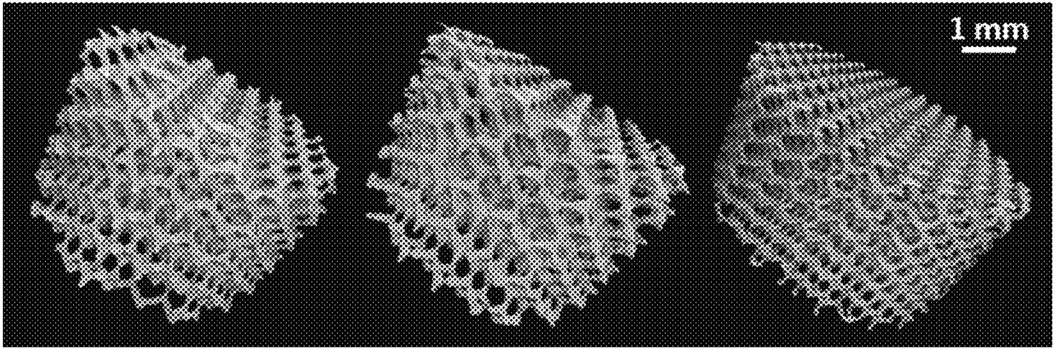
FIG. 2C is a comparison of μ-CT images showing perspective views of scaffolds obtained by 3D printing the structure shown in FIG. 2A above, using three different PPF polymers (from left to right: linear PPF DP10, star PPF DP40, star PPF DP200).
Figure 3A:
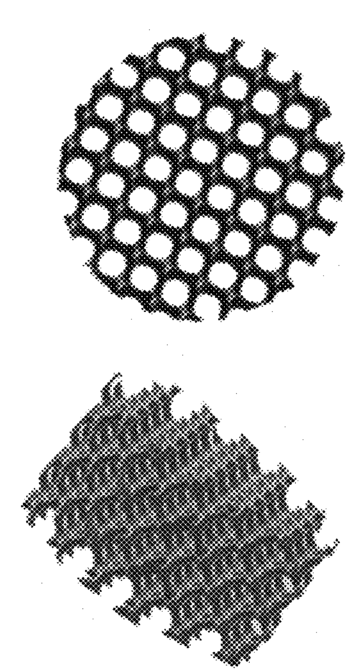
FIG. 3A is a computer-generated image showing a top view (upper) and a perspective view (lower) of a 3D printed structure having Schoen gyroid triply periodic minimal surface with 200 μm strut size, 699 μm pore size, and 88.2% porosity, generated from a CAD file created using MATLAB™ software (The MathWorks, Inc., Natick, MA). (CAD model 2).
Figure 3B:
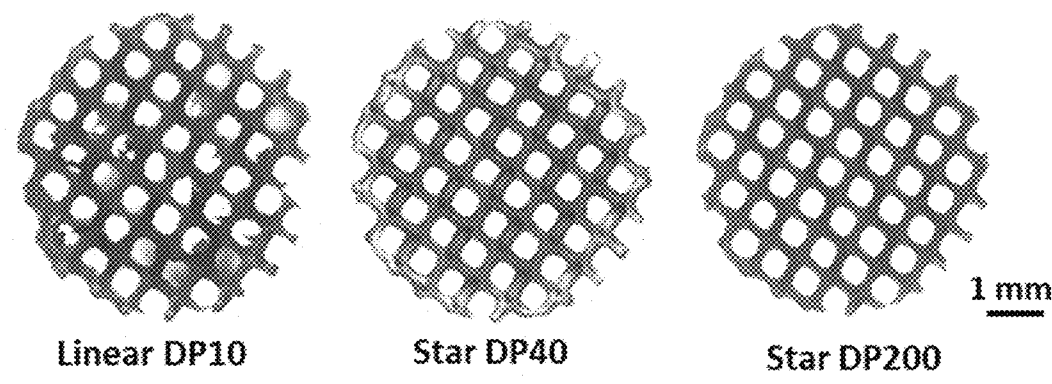
FIG. 3B is a comparison of optical micrographs showing a top view scaffolds obtained by printing the structure of FIG. 3A above, using three different PPF polymers (from left to right: linear PPF DP10, star PPF DP40, star PPF DP200).
Figure 3C:
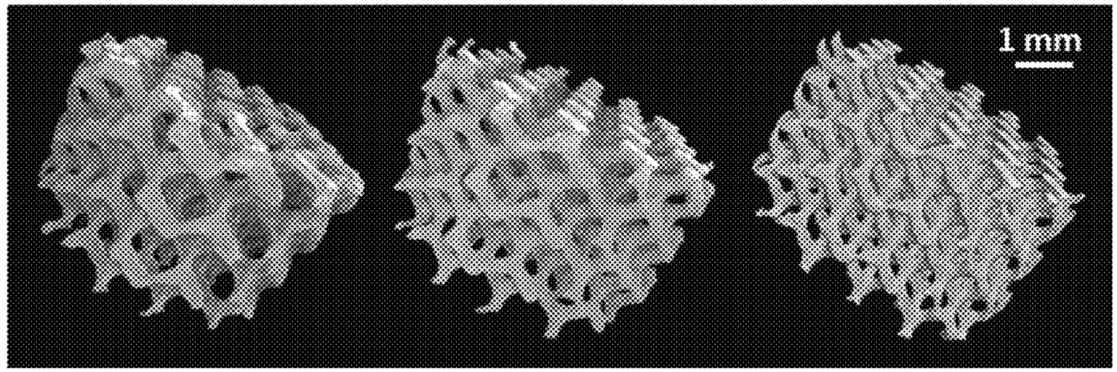
FIG. 3C is a comparison of μ-CT images showing perspective views of scaffolds obtained by 3D printing the structure shown on FIG. 3A above using three different PPF polymers (from left to right: linear PPF DP10, star PPF DP40, star PPF DP200).
Figure 4A:
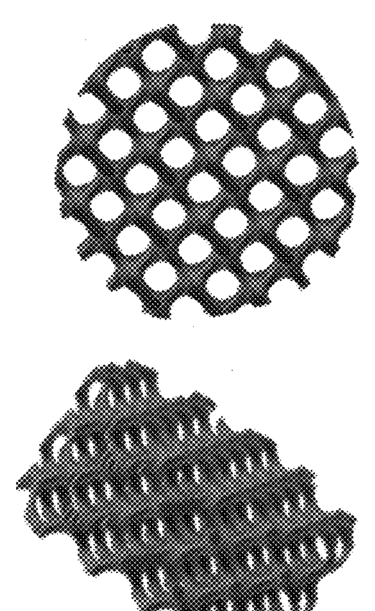
FIG. 4A is a computer-generated image showing a top view (upper) and a perspective view (lower) of a structure having Schoen gyroid triply periodic minimal surface with 240 μm strut size, 838 μm pore size, and 88.2% porosity, generated from a CAD file created using MATLAB™ software (The MathWorks, Inc., Natick, MA). (CAD model 3).
Figure 4B:
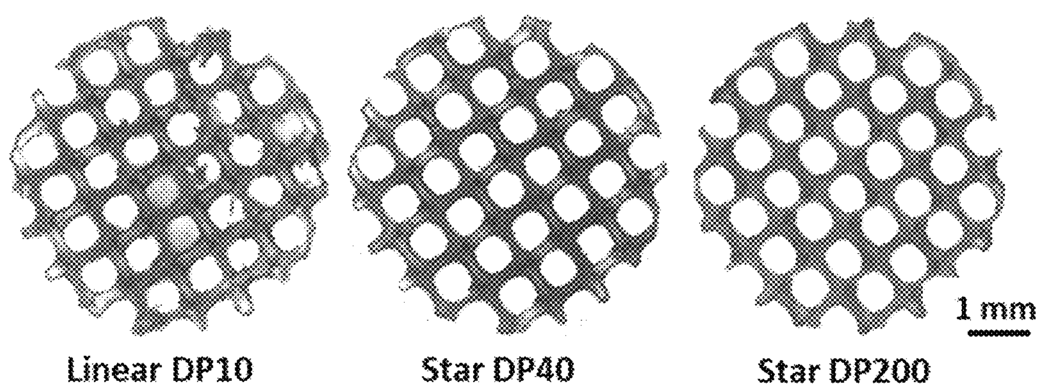
FIG. 4B is a comparison of optical micrographs showing top views scaffolds obtained by 3D printing the structure shown in FIG. 4A above, using three different PPF polymers (from left to right: linear PPF DP10, star PPF DP40, star PPF DP200).
Figure 4C:
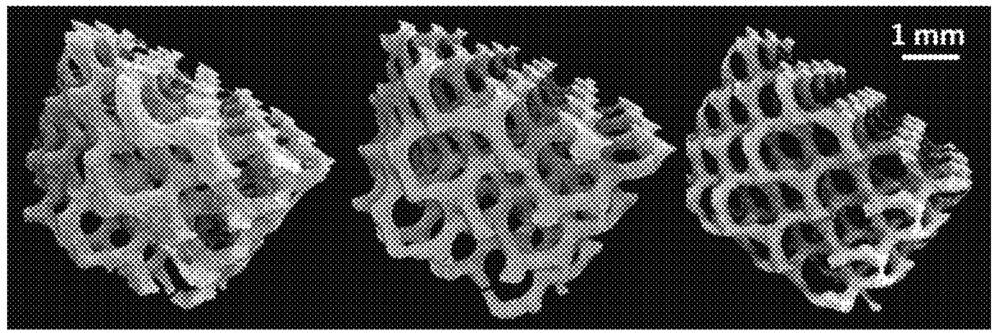
FIG. 4C is a comparison of μ-CT images showing perspective views of scaffolds obtained by 3D printing the structure shown in FIG. 4A above, using three different PPF polymers (from left to right: linear PPF DP10, star PPF DP40, star PPF DP200).
Figure 5A:
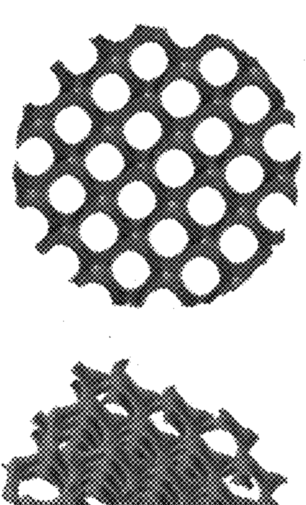
FIG. 5A is a computer-generated image showing a top view (upper) and a perspective view (lower) of a structure having Schoen gyroid triply periodic minimal surface with 280 μm strut size, 978 μm pore size, and 88.2% porosity, generated from a the CAD file created using MATLAB™ software (The MathWorks, Inc., Natick, MA). (CAD model 4).
Figure 5B:
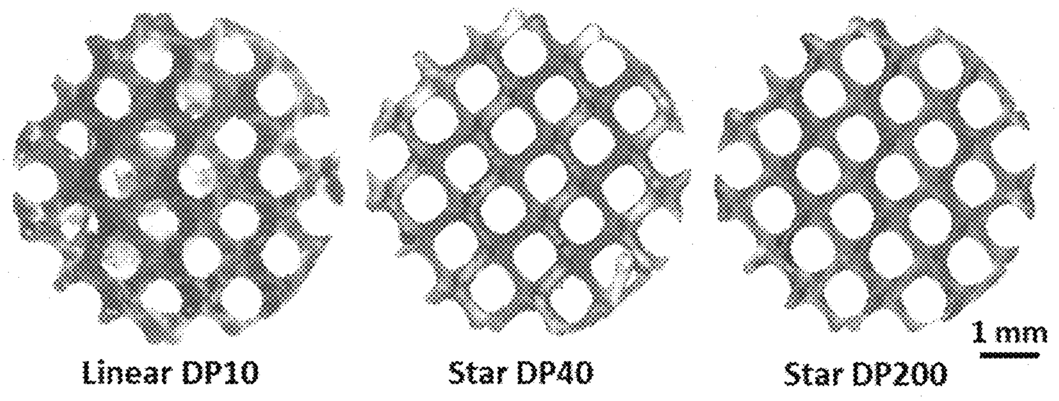
FIG. 5B is a comparison of optical micrographs showing top views scaffolds obtained by 3D printing the structure shown in FIG. 5A above, using three different PPF polymers (from left to right: linear PPF DP10, star PPF DP40, star PPF DP200).
Figure 5C:
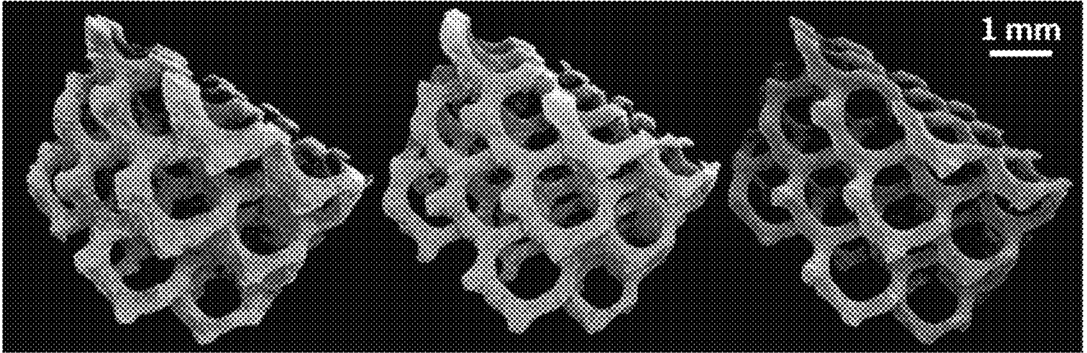
FIG. 5C is a comparison of μ-CT images showing perspective views of scaffolds obtained by 3D printing the structure shown in FIG. 2A above, using three different PPF polymers (from left to right: linear PPF DP10, star PPF DP40, star PPF DP200).

The scaffold dimensions (i.e., diameter and height) were measured with a digital calliper to quantify the shrinkage (FIG. 1B). For the three different PPF, the shrinkage phenomenon induced lower values than expected both in diameter and in height, moreover, lower the strut size, higher this discrepancy. While not wishing to be bound by theory, a possible reason is low strut sizes facilitate the photo-crosslinking and consequently the shrinkage by reducing the chain-to-chain distance. However, no significant differences were triggered by the PPF nature used, except for scaffolds with a strut size of 140 μm for which start PPF DP200 showed a more important shrinkage in height. In addition, the values obtained after 45 min or 90 min of post-curing were similar, which suggests that shrinkage occurred mainly during 3D printing. Due to the reproducibility of the shrinkage observed, as highlighted by the reasonable error bars, the minor disparities between the CAD model and the scaffolds obtained can be predicted and compensated for. Because the internal pore geometry directly impacts the capacity of the scaffold to guide neo-tissues, the vasculature infusion into the defect and can improve cell seeding and/or nutrient flow for ex vivo culturing, it is of primary importance to well characterize the relationship between the resin formulation, the printing parameters and the scaffold architecture. For this purpose, the scaffolds were imaged by optical microscopy to depict the gyroid architecture features in greater detail and to determine their actual strut size.

The structure of the gyroid scaffolds was also characterized by X-ray micro-computed tomography (μ-CT) to determine their total porosity. The corresponding pore sizes were calculated. FIGS. 2A-C, 3A-C, 4A-C and 5A-C show the resulting images for the scaffolds with a strut size of 140, 200, 240 and 280 μm respectively, according the CAD model used. The optical micrographs and μ-CT images of the scaffold based on the linear PPF DP10 revealed a less defined structure and photocrosslinked PPF:DEF resin within the pores, while the scaffolds obtained from the star PPF were well homogeneous with highly reproducible spatial arrangement of pores. The porosity values, the actual strut sizes and the deduced pore sizes are summarized in Table 2. These values highlighted a significant discrepancy between the CAD models and the actual scaffolds for the linear DP10 and on the contrary, a good fidelity between the desired characteristic dimensions and those obtained for the star PPF. This phenomenon can be explained by the larger UV irradiation time/layer needed for the printing of scaffolds with the linear PPF DP10. Indeed, previous studies showed that increasing the irradiation time/layer can cause undesirable "dark" curing occurs, photo-crosslinking of the resin in non-exposed areas, induced by diffusion of radical species. Consequently, the increase in molar mass, thanks to the use of star PPF, allowing a shorter irradiation time/layer, improved the 3D printing fidelity and the manufacturing of well-defined scaffolds with high porosity and thin strut sizes.

TABLE 2

Characterization summary of scaffolds obtained by DLP 3D printing

| | Strut size (μm)[a] | Porosity (%)[b] | Pore size (μm)[c] |
|---|---|---|---|
| CAD model 1 | 140 | 88.2 | 489 |
| Linear PPF DP10 | 131 (±11) | 85.2 | 389 |
| Star PPF DP40 | 142 (±10) | 90.5 | 575 |
| Star PPF DP200 | 141 (±9) | 90.8 | 583 |
| CAD model 2 | 200 | 88.2 | 699 |
| Linear PPF DP10 | 246 (±54) | 81.2 | 613 |
| Star PPF DP40 | 194 (±13) | 88.1 | 674 |
| Star PPF DP200 | 196 (±12) | 86.3 | 616 |
| CAD model 3 | 240 | 88.2 | 838 |
| Linear PPF DP10 | 242 (±26) | 77.9 | 532 |
| Star PPF DP40 | 238 (±17) | 87.3 | 790 |
| Star PPF DP200 | 237 (±11) | 88.3 | 833 |
| CAD model 4 | 280 | 88.2 | 978 |
| Linear PPF DP10 | 393 (±37) | 80.5 | 952 |
| Star PPF DP40 | 286 (±24) | 87.8 | 976 |
| Star PPF DP200 | 275 (±11) | 87.6 | 928 |

[a]obtained by optical microscopy, analyses using ImageJ software based on two scaffolds and 30 measurements.
[b]obtained by μ-CT.
[c]calculated.

Figure 6A:
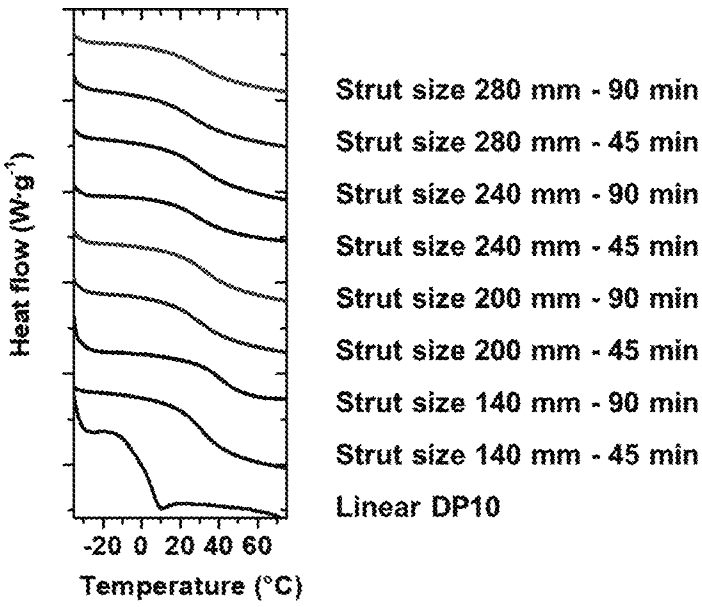
FIGS. 6A-C are the differential scanning calorimetry (DSC) traces for scaffolds made using linear PPF DP10 polymer (FIG. 6A), PPF star DP40 polymers (FIG. 6B) and PPF star DP200 polymers of various strut sizes at post-curing times of 45 and 90 min. The temperature scan rate was 10° C.·min$^{-1}$.
Figure 6B:
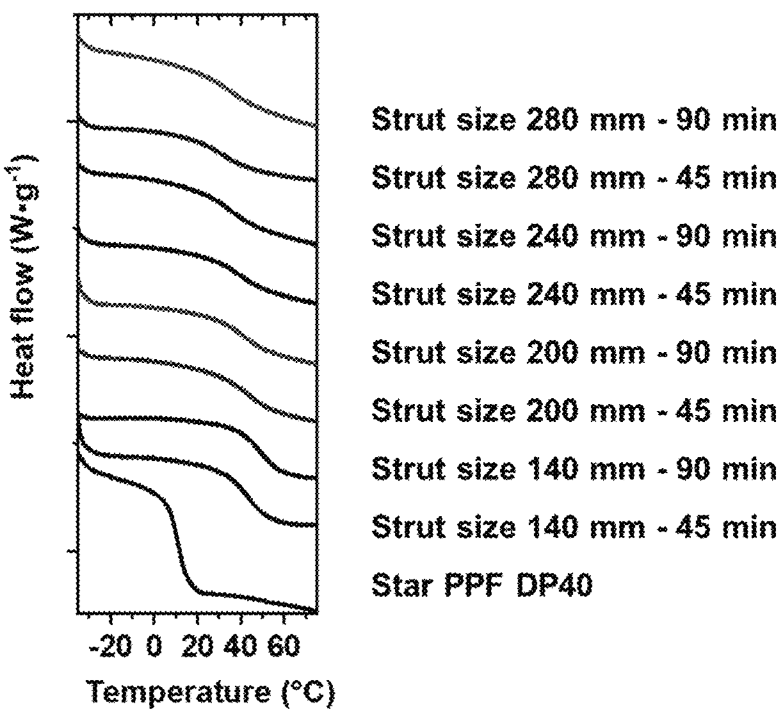
Figure 6C:
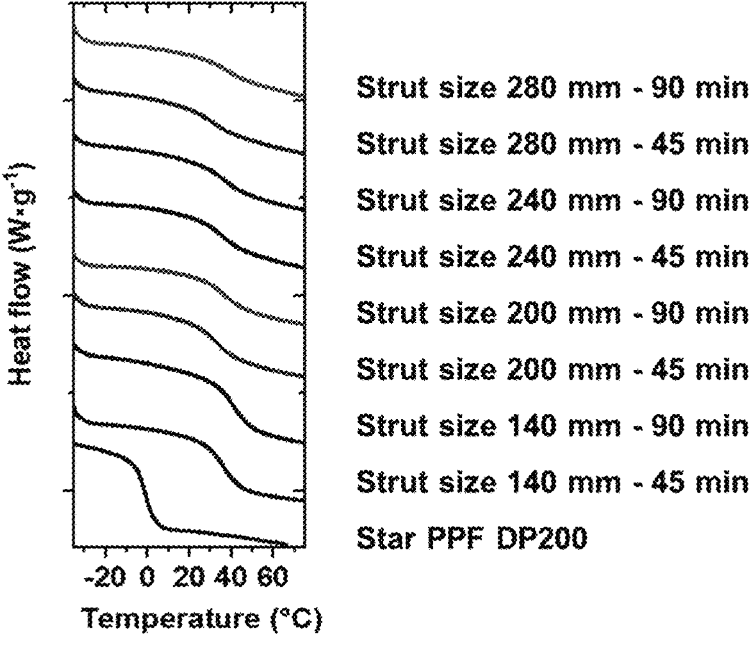

Glass transition temperature ($T_g$) values of linear, star PPF copolymers and resulting scaffolds were determined using differential scanning calorimetry (DSC) (FIG. 6) and reported in Table 3. PPF polymers display $T_g$ values of 2.5° C. for the linear DP10 and 11° C. and −2.2° C. for the star PPF DP40 and DP200 respectively. This was expected as the star PPF DP40 corresponds to four chain of linear DP10 covalently bonded which lead to decrease chain mobility and an increase in $T_g$. Unlike linear PPF oligomers for which $T_g$ values increased with the $\overline{M_n}$, the star PPF showed a decrease in $T_g$ values with the $\overline{M_n}$ increase. The scaffolds presented higher $T_g$ than their corresponding PPF copolymer with values falling between 26.6-40.8° C. for the linear PPF DP10, 32.0-49.1° C. for the star PPF DP40 and 29.4-41.0° C. for the star PPF DP200 respectively. It was generally observed that the $T_g$ increases when the post-curing time increases, indicating lower chain mobility due to higher crosslinking ratio. Interestingly, a strut size increase induced a $T_g$ decrease indicating a lower crosslinking ratio, due to the lower penetration of UV light into the strut sizes.

TABLE 3

$T_g$ values of the PPF copolymers and corresponding scaffolds obtained by DSC.

| | | $T_{g\ (scaffolds)}$ (° C.) | |
|---|---|---|---|
| Polymer | Strut size (μm) | Post-curing 45 min | Post-curing 90 min |
| Linear DP10 ($T_g$ = 2.5° C.) | 140 | 30.8 | 40.8 |
| | 200 | 29.1 | 32.1 |
| | 240 | 28.8 | 29.8 |
| | 280 | 26.6 | 27.9 |
| Star DP40 ($T_g$ = 11° C.) | 140 | 42.8 | 49.1 |
| | 200 | 42.0 | 42.9 |
| | 240 | 36.0 | 38.0 |
| | 280 | 32.0 | 35.5 |
| Star DP200 ($T_g$ = −2.2° C.) | 140 | 35.4 | 41.0 |
| | 200 | 34.9 | 37.0 |
| | 240 | 31.9 | 36.5 |
| | 280 | 29.4 | 34.1 |

Example 4

Mechanical Properties of Gyroids Scaffolds Based on Linear PPF DP10 and PPF Stars DP40 and DP200

Figure 7A:
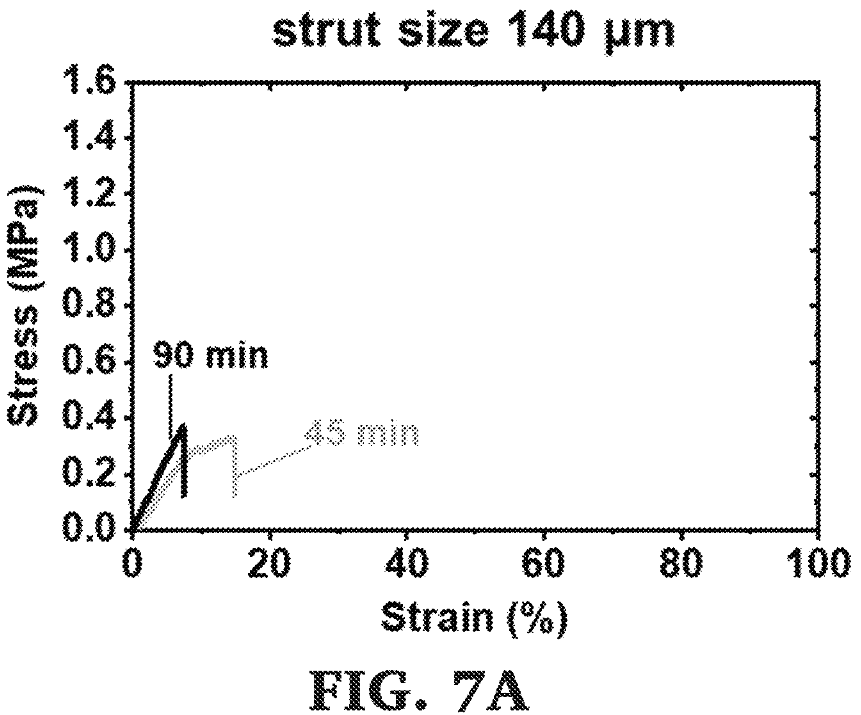
FIGS. 7A-D are charts comparing the post-curing stress versus strain curves after 45 min and 90 min for 3D printed gyroid scaffolds formed using linear PPF DP10 with a strut size of 140 μm (FIG. 7A), 200 μm (FIG. 7B), 240 μm (FIG. 7C) and 280 μm (FIG. 7H).
Figure 7B:
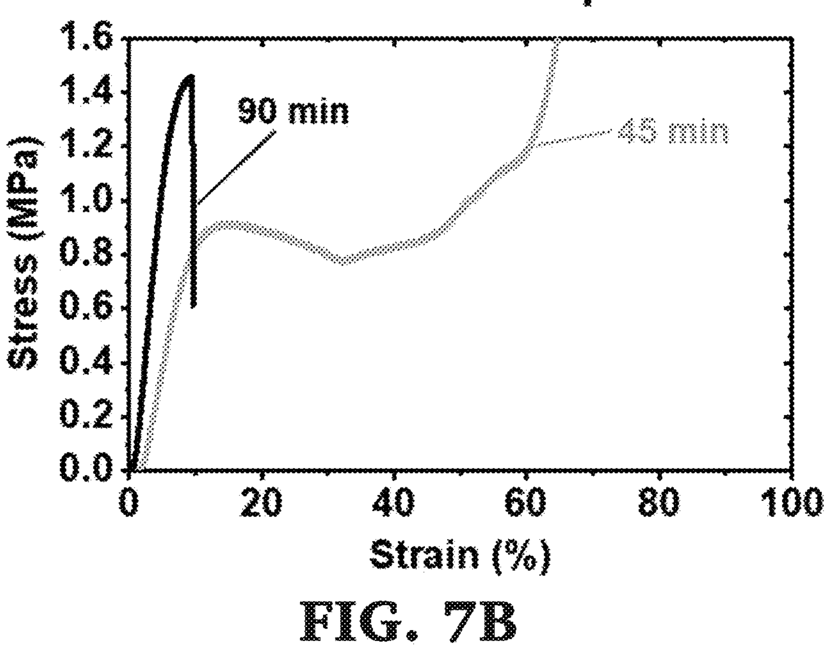
Figure 7C:
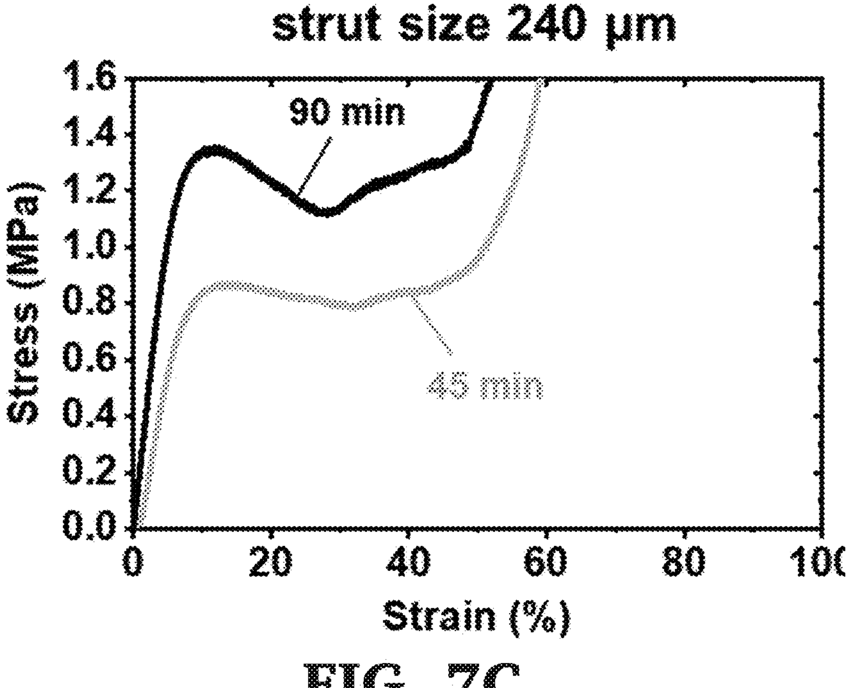
Figure 7D:
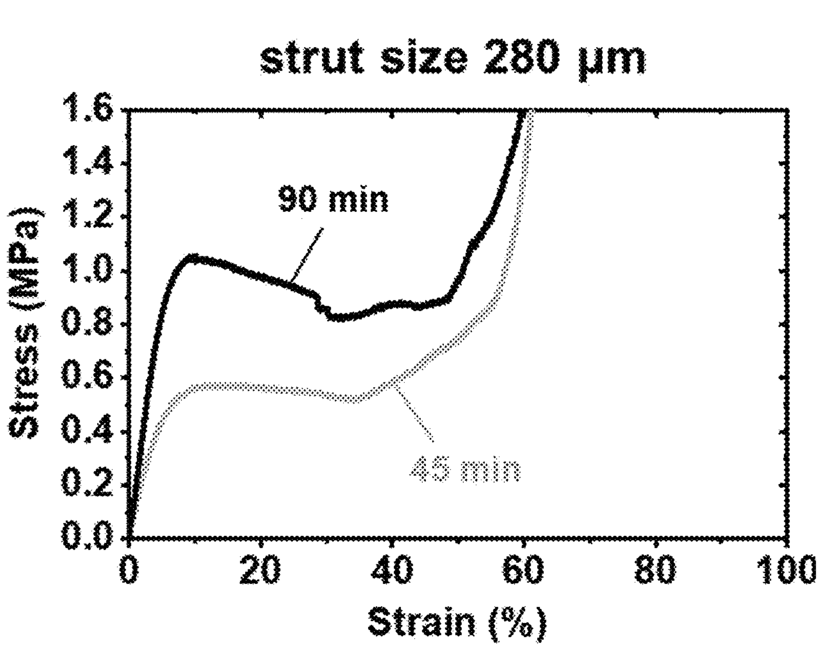
Figure 7E:
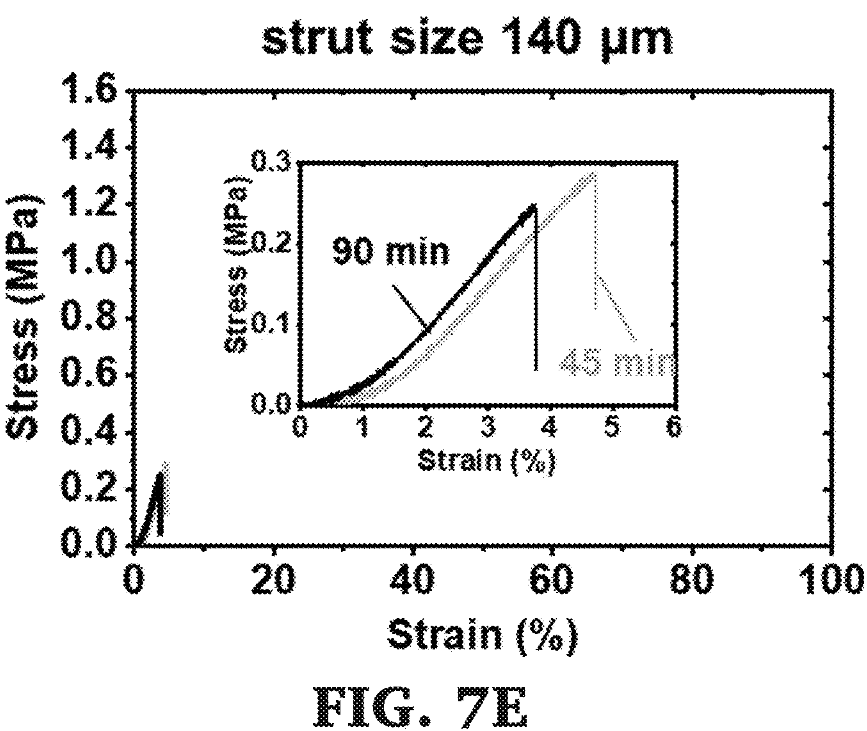
FIGS. 7E-H are charts comparing the post-curing stress versus strain curves after 45 min and 90 min for 3D printed gyroid scaffolds 3D formed using PPF star DP40 and having a strut size of 140 μm (FIG. 7E), 200 μm (FIG. 7F), 240 μm (FIG. 7G) and 280 μm (FIG. 7H).
Figure 7F:
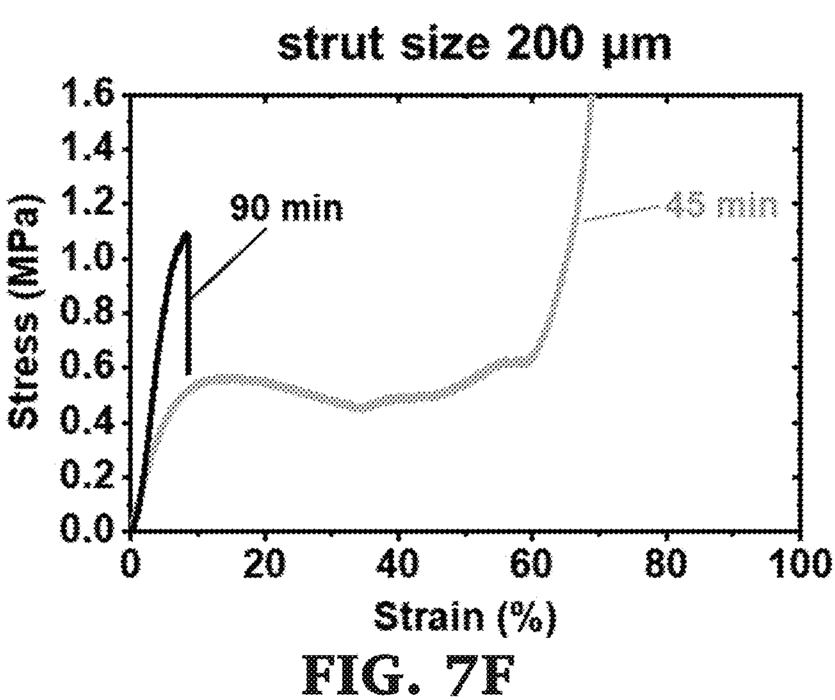
Figure 7G:
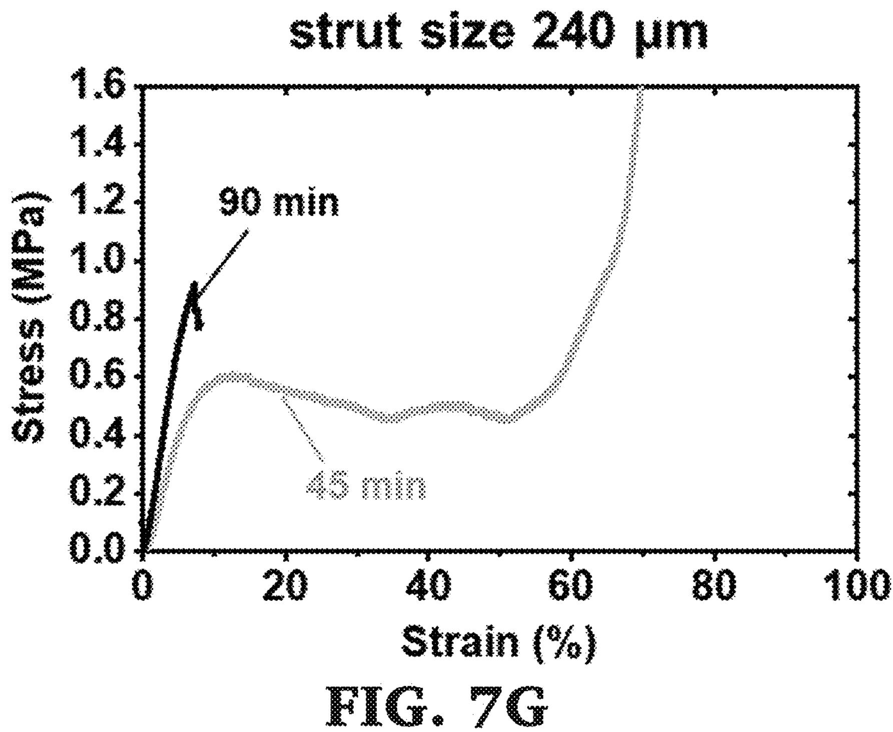
Figure 7H:
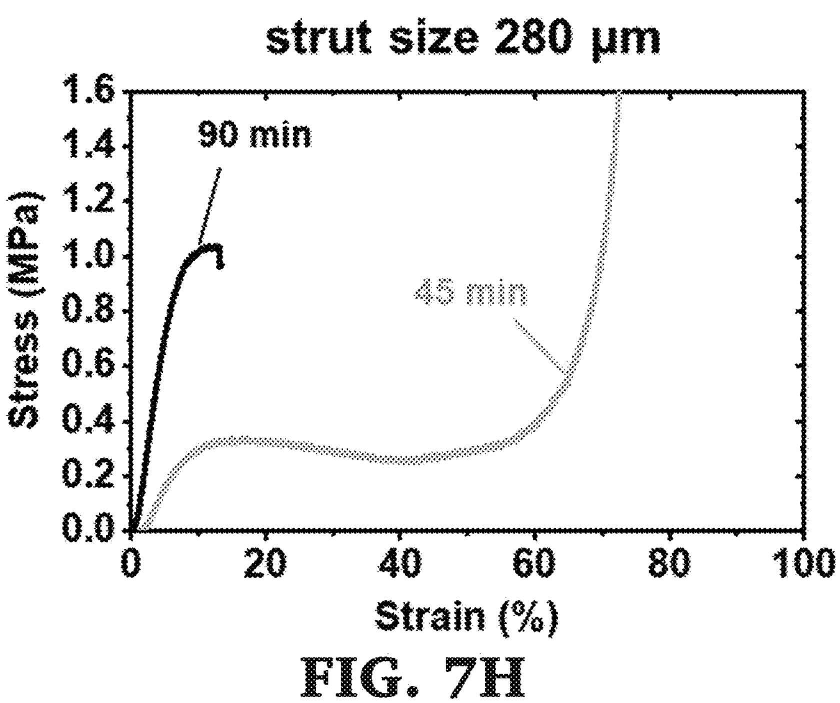
Figure 7I:
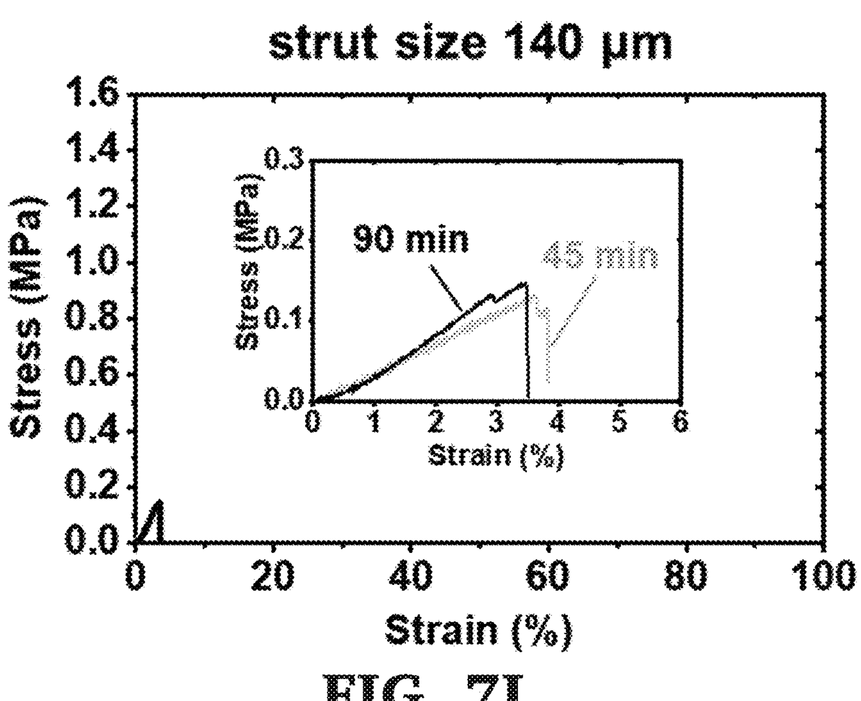
FIG. 7I-L are charts comparing the post-curing stress versus strain curves after 45 min and 90 min for 3D printed gyroid scaffolds 3D formed using PPF star DP200 and having a strut size of 140 μm (FIG. 7I), 200 μm (FIG. 7J), 240 μm (FIG. 7K) and 280 μm (FIG. 7L).
Figure 7J:
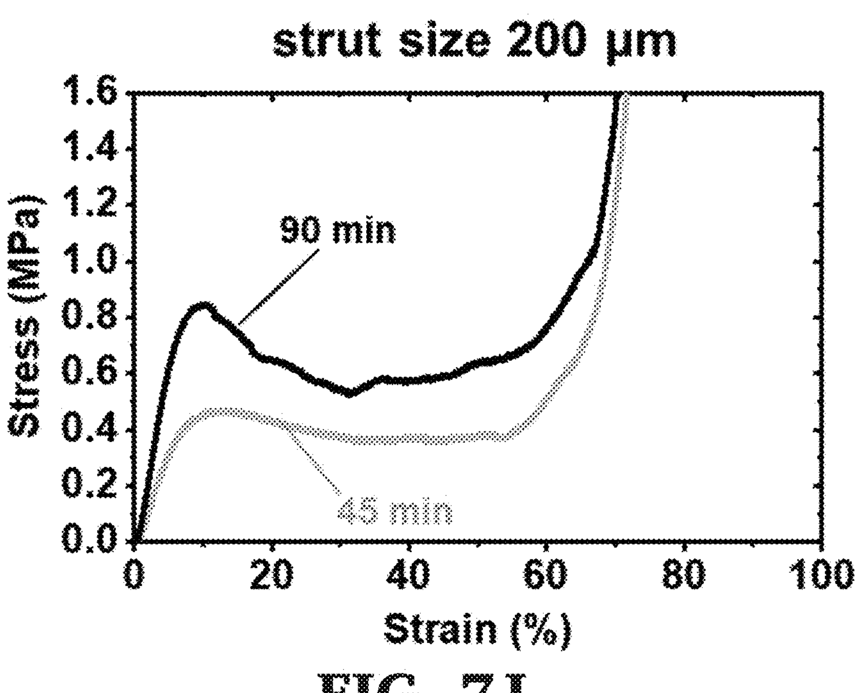
Figure 7K:
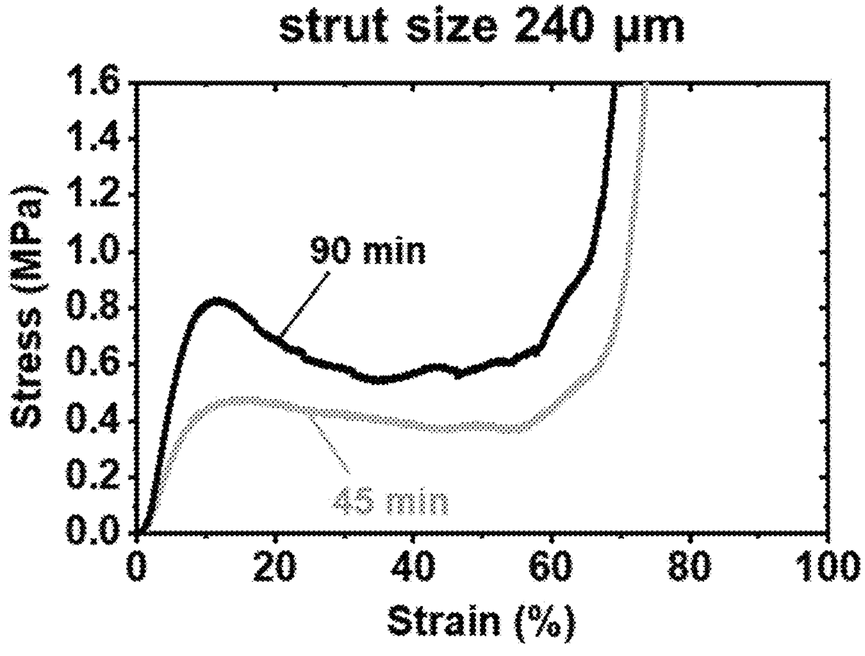
Figure 7L:
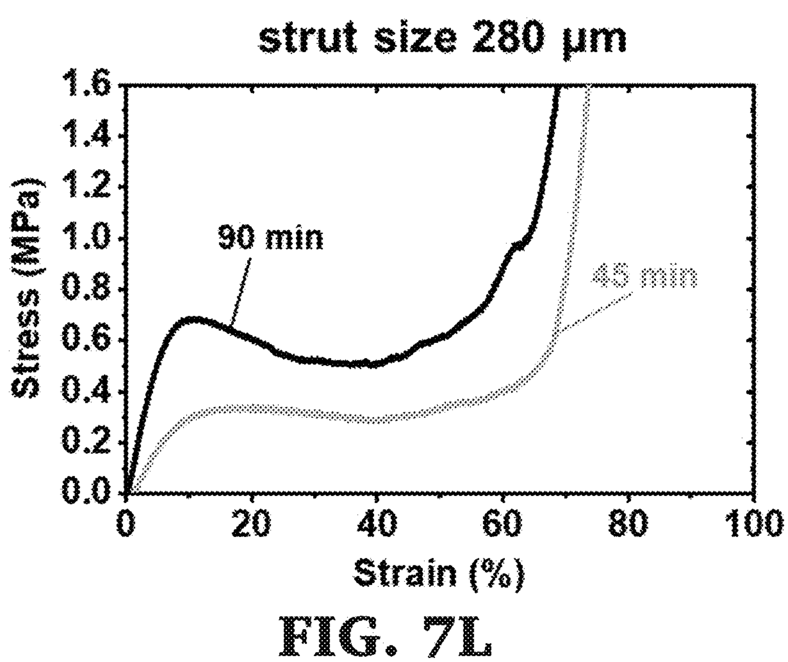
Figure 8:
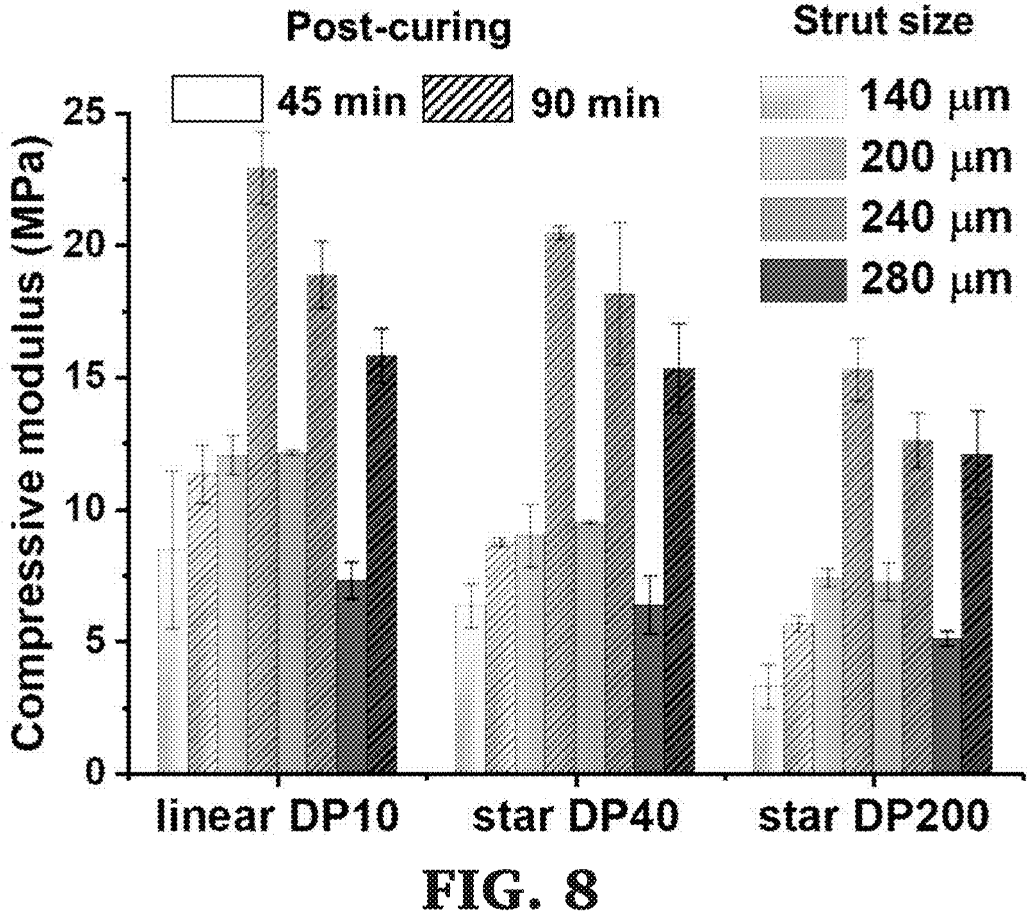
FIG. 8 is the bar diagram showing compressive modulus values obtained for 3D printed scaffolds at different strut sizes (140, 200, 240 or 280 μm) and post-curing times under UV exposure (45 and 90 min).

Compression tests were conducted to investigate the mechanical properties of these scaffolds at room temperature. Scaffolds were characterized by monitoring stress and strain throughout the experiment (FIGS. 7A-L). The compressive moduli were calculated using the slope of linear fitting in the first linear regime. The reported results are average values from four individual measurements and the associated errors are the standard deviations (FIG. 8). According the PPF used, the scaffold architecture and the post-curing time, the stress versus strain curves highlighted completely different behaviors (FIGS. 7A-L). The scaffolds with the lowest strut size, i.e., 140 μm, exhibited brittle fracture, irrespective of the PPF used or the post-curing time (FIGS. 7A, 7E and 7I). All the other scaffolds that underwent a short post-curing time of 45 min, supported the applied load with no apparent sudden failure. Indeed, most of the curves were characterized by a decline in the stress values corresponding to a softening region and then appearance of humps showing successive collapse of pores in planes perpendicular to loading direction (z), which are the signature of a low-strain failure. Nevertheless, for the scaffolds based on star PPF DP40 and PPF DP200 and strut size of 280 μm (respectively FIGS. 7H and 7L), the curves showed an initial linear elastic deformation after which stress non-linearly increased with the applied strain to reach a plateau regime, highlighting lack of failure and stretching of struts. Upon further compression, the structure grew stronger after the densification as shown by the slope increase. This densification step appeared earlier for the linear DP10, in a 25-40% strain range, than for the star PPF, in a 45-63% strain range, indicating higher elasticity of star PPF DP40 and 200 polymers themselves than linear PPF DP10. After a post-curing of 90 min, the scaffolds of linear DP10 and strut sizes 140 and 200 μm and all the scaffolds of star PPF DP40 exhibited brittle fracture while the other scaffolds of linear DP10 and star DP200 displayed only a low-strain failure with successive pore collapses. For these scaffolds obtained after a longer post-curing, the densification occurred earlier than those after only 45 min, due to higher crosslinking ratios coupled with higher $T_g$ values. Compressive modulus varied between 3.26±0.83 MPa and 12.3±0.74 MPa for scaffolds that underwent 45 min post-curing time, and between 5.65±0.30 MPa and 22.9±1.35 MPa for scaffolds after 90 min post-curing time, so compressive modulus was generally found to be the greatest after a longer post-cure treatment. Consequently, a longer post-curing time can increase the compression modulus while make the scaffolds more brittle.

Example 5

Shape Memory Properties of Gyroids Scaffolds Based on Linear PPF DP10 and PPF Stars DP40 and DP200

Figure 9A:
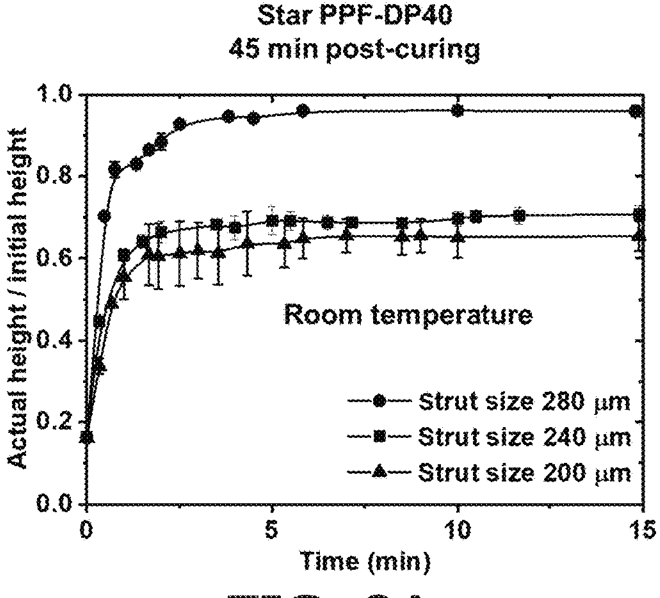
FIG. 9A is a graph showing the shape recovery at room temperature after compression for 3D printed scaffolds after 45 min of post-curing: actual height/initial height ratio versus time for scaffolds based on star PPF DP40.
Figure 9B:
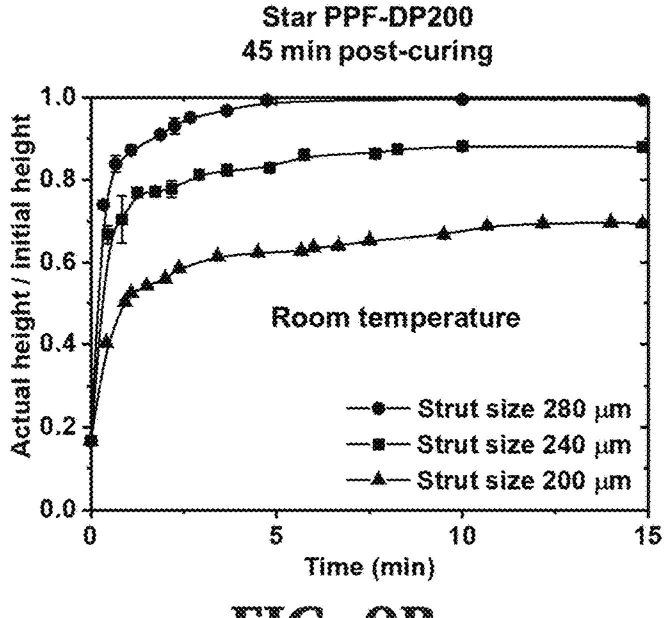
FIG. 9B is a graph showing the shape recovery at room temperature after compression for the 3D printed scaffolds after 45 min of post-curing: actual height/initial height ratio versus time for scaffolds based on star PPF DP200.
Figure 9C:
FIG. 9C is a series of images taken at regular time intervals of a 3D printed scaffold according to one or more embodiments of the present invention (four-arm PPF DP200, strut size 280 μm, 45 min post-curing) showing height changes over time during the recovery.
Figure 10A:
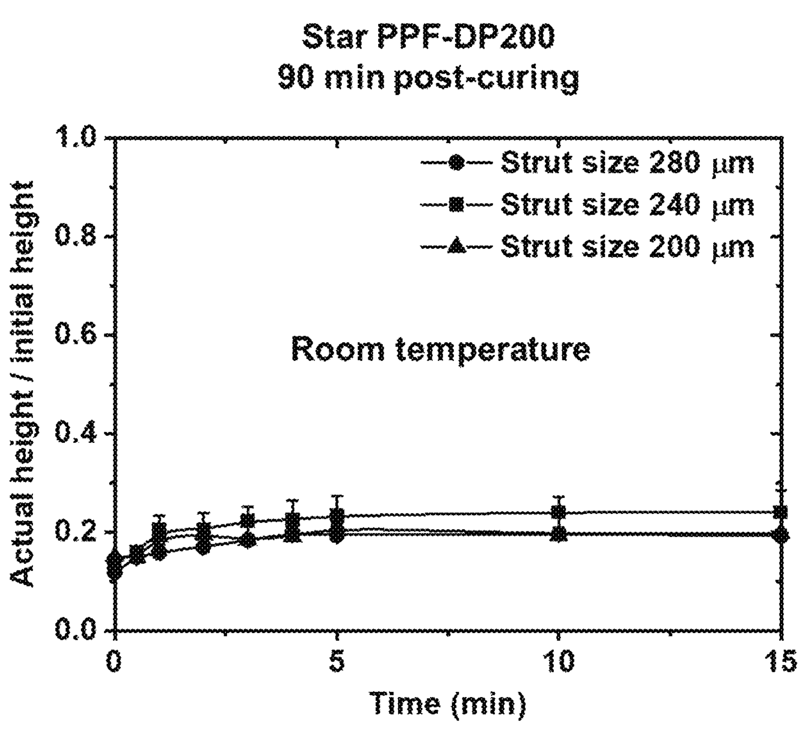
FIG. 10A is a graph showing shape recovery at room temperature after compression for 3D printed scaffolds after 90 min of post-curing: actual height/initial height ratio versus time for scaffolds based on star PPF DP200.
Figure 10B:
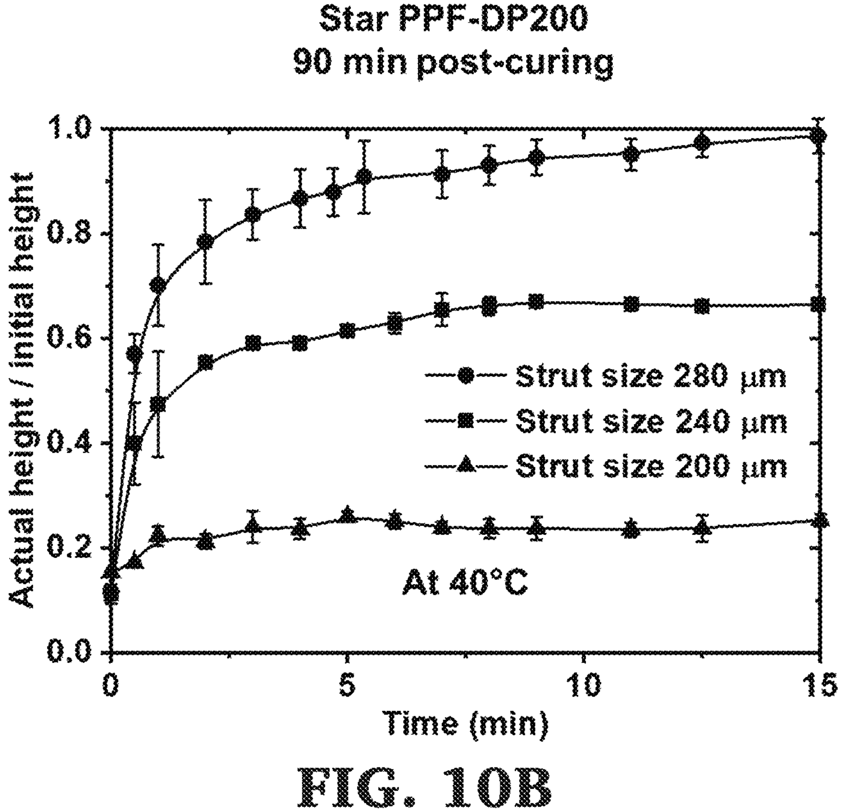
FIG. 10B is a graph showing shape recovery at 40° C. after compression for 3D printed scaffolds after 90 min of post-curing: actual height/initial height ratio versus time for scaffolds based on star PPF DP200.
Figure 11:
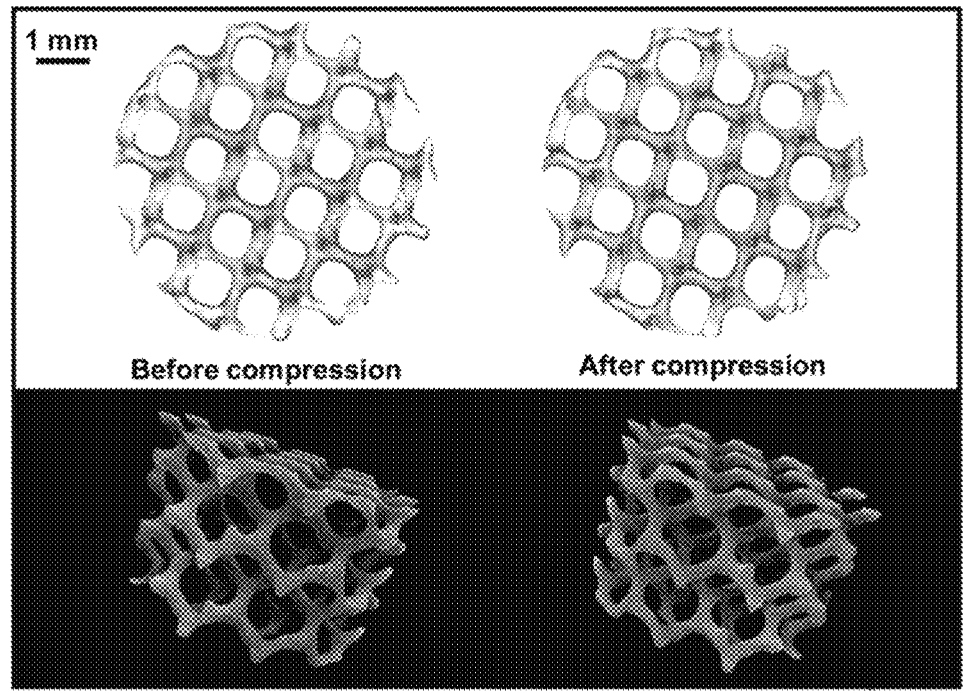
FIG. 11 is a comparison of optical micrographs of the top (upper) and corresponding μ-CT images (lower) of the 3D printed scaffolds of star PPF DP200 before (left) and after (right) compression and complete recovery.

To evaluate shape-recovery of the scaffolds that did not show failure, the height of the scaffolds was measured overtime just after compression and the actual height/initial height ratio plotted with time (FIG. 9A-B). At room temperature, scaffolds of PPF stars DP40 with strut sizes of 200 and 240 μm showed partial recovery, about 60% and for strut size of 280 μm an almost complete recovery, about 95% in 5 min (FIG. 9A). In a different way, scaffolds of PPF stars DP200 showed better recoveries as the strut size increased, indeed, the scaffold with a 200 μm strut size reached 75% of recovery, while strut sizes of 240 and 280 μm led to 90% and 100% of recovery in 5 min respectively (FIG. 9B). This shape-recovery capacity can be described as the result of the scaffold state after compression; indeed, scaffolds that showed an elastic deformation and consequently no failure were able to recover their shape once the compressive force was removed. Then, the recovery properties of the scaffolds based on PPF stars DP200 after 90 min of post-curing time were investigated both at room temperature and at 40° C. (FIGS. 10A-B). At room temperature, the scaffolds were not able to recover their shape (FIG. 10A), while, at 40° C., PPF stars DP200 showed a better recovery as the strut size increased, the scaffold with a 200 μm strut presented a poor recovery, similar to that obtained at room temperature, while strut sizes of 240 and 280 μm led to 65% and 100% of recovery in 15 min respectively (FIG. 10B). Scaffolds of PPF stars DP200 were characterized by optical microscopy and μ-CT before compression and after compression and total recovery (FIG. 11). Pictures showed very similar structures and no change in the porosity value was observed. Consequently, these high porosity scaffolds, based on PPF stars DP200 and with strut size of 280 μm showed good shape-memory behavior after compression. Their recovery behavior can occur at room temperature or higher temperature, here 40° C., depending on the duration of the post-curing step leading to various elasticities. Therefore, the mechanical characteristics of PPF scaffolds are the consequence of combined properties: those of the different PPF, the crosslinking ratios tuned by changing the post-curing duration, and the varying gyroid architectures styles. On the contrary, a star PPF DP200 showed lower $T_g$ values, both for the polymer and for the scaffolds, this trend had a direct impact on the mechanical behavior, fracture or recovery of specimens.

What is claimed is:

1. A resorbable star poly(propylene fumarate) (PPF) 4D printed structure having a first shape, a second compressed shape, and a third recovered shape, wherein said resorbable star PPF 4D printed structure will, when compressed from said first shape to said second compressed shape, transform to said third recovered shape over a predetermined time interval or at a predetermined temperature.

2. The resorbable star PPF 4D printed structure of claim 1 comprising a multi-arm PPF star polymer formed by controlled ring opening copolymerization (ROCOP) of a cyclic anhydride and an epoxide using a catalyst and a multi-functional alcohol initiator, said multi-arm PPF star polymer having a degree of polymerization of from about 40 to about 200.

3. The resorbable star PPF 4D printed structure of claim 2 wherein the cyclic anhydride is at least one of maleic anhydride and succinic anhydride, with the proviso that the cyclic anhydride contain at least some maleic anhydride.

4. The resorbable star PPF 4D printed structure of claim 2 wherein the epoxide is propylene oxide.

5. The resorbable star PPF 4D printed structure of claim 2 wherein multi-arm PPF star polymer formed by controlled ring opening copolymerization (ROCOP) of maleic anhydride and propylene oxide using a catalyst and a multi-functional alcohol initiator, said multi-arm PPF star polymer having a degree of polymerization of from about 40 to about 200.

6. The resorbable star PPF 4D printed structure of claim 2 wherein multi-arm PPF star polymer formed by controlled ring opening copolymerization (ROCOP) of succinic anhydride and propylene oxide using a catalyst and a multi-functional alcohol initiator, said multi-arm PPF star polymer having a degree of polymerization of from about 40 to about 200.

7. The resorbable star PPF 4D printed structure of claim 1 wherein multi-arm PPF star polymer has from 3 to 5 arms.

8. The resorbable star PPF 4D printed structure of claim 1 having a glass transition temperature ($T_g$) of from about from about 10° C. to about 60° C.

9. The resorbable star PPF 4D printed structure of claim 1 having a compressive modulus of from about 2 MPa to about 40 MPa.

10. The resorbable star PPF 4D printed structure of claim 1 wherein the first shape is a gyroid having a substantially uniform pore geometry and porosity.

11. The resorbable star PPF 4D printed structure of claim 10 having a plurality of struts with a strut size of from about 100 microns to about 500 microns.

12. The resorbable star PPF 4D printed structure of claim 11 wherein the struts are regularly spaced.

13. The resorbable star PPF 4D printed structure of claim 11 wherein the struts are anisotropic.

14. The resorbable star PPF 4D printed structure of claim 10 having a porosity of from about 30% to about 92.

15. The resorbable star PPF 4D printed structure of claim 10 having a pore size of from about 50 microns to about 2500 microns.

16. The resorbable star PPF 4D printed structure of claim 1 wherein said resorbable star PPF 4D printed structure becomes more dense under compression.

17. The resorbable star PPF 4D printed structure of claim 1 wherein said resorbable star PPF 4D printed structure has been post-cured with UV irradiation after printing.

18. The resorbable star PPF 4D printed structure of claim 17 wherein said resorbable star PPF 4D printed structure has been post-cured for from about 1 min to about 1200 min with UV irradiation after printing.

19. The resorbable star PPF 4D printed structure of claim 1 wherein said predetermined time interval is from about 1 h to about 72 h at ambient temperature.

20. The resorbable star PPF 4D printed structure of claim 1 wherein said predetermined time interval is from about 1 min to about 60 min at ambient temperature.

21. The resorbable star PPF 4D printed structure of claim 1 wherein said predetermined temperature is from about 20° C. to about 50° C.

22. The resorbable star PPF 4D printed structure of claim 1 wherein said predetermined temperature is from about 20° C. to about 45° C.

23. The resorbable star PPF 4D printed structure of claim 1 wherein said predetermined temperature is from about 30° C. to about 42° C.

24. The resorbable star PPF 4D printed structure of claim 1 wherein said predetermined temperature is from about 30° C. to about 40° C.

25. The resorbable star PPF 4D printed structure of claim 1 wherein said predetermined temperature is the body temperature of a human or other mammal into the body of which said resorbable star PPF 4D printed structure is implanted or inserted.

26. The resorbable star PPF 4D printed structure of claim 1 having tunable degradation and resorbability.

27. The resorbable star PPF 4D printed structure of claim 26 wherein the resorbability may be controlled by varying molar mass of the multi-arm PPF star polymer.

28. The resorbable star PPF 4D printed structure of claim 1 wherein said first shape and said third recovered shape are the same.

29. The resorbable star PPF 4D printed structure of claim 1 wherein said third recovered shape is from about 65% and 100% of said first shape.

30. The resorbable star PPF 4D printed structure of claim 1 further comprising one or more linear PPF polymer.

31. The resorbable star PPF 4D printed structure of claim 1 comprising a bone scaffold, vascular stent, kidney stent, urethral stent, colitis stent, esophageal stent, colon stent, intestinal stent, or venous stent.

32. A method of making the resorbable star poly (propylene fumarate) (PPF) 4D printed structure of claim 1 comprising:

A) preparing a 3D printable resin comprising a star PPF polymer;

B) printing a 3D structure from the star PPF polymer containing 3D printable resin using a suitable 3D printer; and C) post-curing the 3D printed structure by UV irradiation.

33. The method of claim 32 wherein said a star PPF polymer comprises a multi-arm PPF star polymer formed by controlled ring opening copolymerization (ROCOP) of a cyclic anhydride with an epoxide using a multi-functional alcohol initiator and a catalyst and having a degree of polymerization of from about 40 to about 200.

34. The method of claim 33 wherein said cyclic anhydride is at least one of maleic anhydride and succinic anhydride and said epoxide is propylene oxide.

35. The method of claim 33 wherein said multi-arm PPF star polymer has from 3 to 5 PPF arms connected at a central core, said central core comprising the residue of the multi-functional alcohol initiator.

36. The method of claim 32 wherein said 3D printable resin comprises a star PPF polymer having from 3 to 5 arms, diethyl fumarate (DEF), and a photoinitiator.

37. The method of claim 32 wherein said suitable 3D printer is a continuous digital Light processing (cDLP) 3D printer.

38. The method of claim 32 wherein said step of post-curing comprises irradiating said 3D printed structure with UV light for from about 1 min to about 1200 min.

39. The method of claim 32 wherein said 3D structure is a gyroid having a substantially uniform pore geometry and porosity.

40. The method of claim 39 wherein said 3D structure is a gyroid having a plurality of regularly placed struts with a strut size of from about 100 to about 500.

41. The method of claim 39 wherein said 3D structure is a gyroid having a porosity of from about 30% to about 92%.

42. The method of claim 39 wherein said 3D structure is a gyroid having a pore size of from about 50 microns to about 2500 microns.

* * * * *